(12) United States Patent
Schaufele

(10) Patent No.: US 10,324,099 B2
(45) Date of Patent: Jun. 18, 2019

(54) ULTRASENSITIVE ANDROGEN RECEPTOR BIOASSAY

(71) Applicant: The Regents of the University of California, Oakland, CA (US)

(72) Inventor: Fred Schaufele, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 134 days.

(21) Appl. No.: 15/128,652

(22) PCT Filed: Mar. 24, 2015

(86) PCT No.: PCT/US2015/022301
§ 371 (c)(1),
(2) Date: Sep. 23, 2016

(87) PCT Pub. No.: WO2015/148549
PCT Pub. Date: Oct. 1, 2015

(65) Prior Publication Data
US 2017/0176467 A1    Jun. 22, 2017

Related U.S. Application Data

(60) Provisional application No. 61/970,883, filed on Mar. 26, 2014.

(51) Int. Cl.
| | | |
|---|---|---|
| G01N 33/53 | (2006.01) | |
| G01N 33/74 | (2006.01) | |
| C12N 15/85 | (2006.01) | |
| C12Q 1/68 | (2018.01) | |
| C07K 14/72 | (2006.01) | |
| C07K 14/435 | (2006.01) | |
| C12N 15/62 | (2006.01) | |

(52) U.S. Cl.
CPC ..... *G01N 33/743* (2013.01); *C07K 14/43595* (2013.01); *C07K 14/721* (2013.01); *C12N 15/625* (2013.01); *C12N 15/85* (2013.01); *C12Q 1/68* (2013.01); *C07K 2319/09* (2013.01); *C07K 2319/60* (2013.01); *G01N 2333/723* (2013.01)

(58) Field of Classification Search
None
See application file for complete search history.

(56) References Cited

U.S. PATENT DOCUMENTS

2016/0243084 A1 * 8/2016 Taylor .................. A61K 9/4866

OTHER PUBLICATIONS

Kofoed et al, "Dimerization between aequorea fluorescent proteins does not affect interaction between tagged estrogen receptors in living cells", Journal of Biomedical Optics, vol. 13, No. 3, p. 031207 (internal pp. 1-27) 2008. See pp. 19.
Schaufele et al., "The structural basis of androgen receptor activation: intromolecular and intermolecular amino-carboxy interactions", Proceedings of the National Academy of Sciences of the United States of America, vol. 102, No. 28, pp. 9802-9807 (2005),—whole document.
Tan et al., "Dehydroepiandrosterone activates mutant androgen receptors expressed in the androgen-dependent human prostate cancer xenograft CWR22 and LNCaP cells", Molecular endocrinology, vol. 11, No. 4, pp. 450-459 (1997), /see oage 455.
Lange et al., "Classical nuclear localization signals: definition, function, and interactioin with importing alpha", Journal of Biological Chemistry, vol. 282, No. 8, pp. 5101-5105 (2207). See p. 5101.
Shaner et al., "Advances in fluorescent protein technology", Journal of Cell Science, vol. 120, No. 24, pp. 4247-4260 (2007), see abstract; Table 1.
Johnson et al, 2001. Androgen receptor stabilization in recurrent prostate cancer is associated with hypersensitivity to low androgen. Cancer Res. 61(7):2892-8. See pp. 2896-2897.

* cited by examiner

*Primary Examiner* — Michael D Pak

(57) ABSTRACT

Provided herein are novel assays for the measurement of androgens such as testosterone in a sample. The assays utilize sensitive androgen receptor mutants and have much greater sensitivity than assays based on wild-type androgen receptors. The assays of the invention can detect androgens at concentrations as low as 1 ng/dl in serum, urine, environmental samples and other samples. The invention encompasses novel assay methods as well as nucleic acid sequences, proteins, and cells. Advantageously, the assays provide a measure of physiologically relevant androgen concentrations in a sample, taking into account the presence of androgen-binding factors or anti-androgen drugs in serum.

15 Claims, No Drawings
Specification includes a Sequence Listing.

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Artificial linker sequence

<400> SEQUENCE: 1

Lys Asp Pro Pro Val Ala Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Artificial linker sequence

<400> SEQUENCE: 2

Ser Gly Leu Arg Ser Arg Ala Thr
1               5

<210> SEQ ID NO 3
<211> LENGTH: 1407
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of human V715M mutant androgen
      receptor with two yellow fluorescent proteins, one each linked
      at the carboxy and amino termini of the mutant androgen
      sequence
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (1236)..(1236)
<223> OTHER INFORMATION: Any amino acid

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Xaa Leu Gln Cys Phe Ala Arg Tyr Pro Asp His Met Lys Arg His Asp
65                  70                  75                  80

Phe Phe Lys Ser Ala Met Pro Glu Gly Tyr Val Gln Glu Arg Thr Ile
                85                  90                  95

Phe Phe Lys Asp Asp Gly Asn Tyr Lys Thr Arg Ala Glu Val Lys Phe
            100                 105                 110

Glu Gly Asp Thr Leu Val Asn Arg Ile Glu Leu Lys Gly Ile Asp Phe
        115                 120                 125

Lys Glu Asp Gly Asn Ile Leu Gly His Lys Leu Glu Tyr Asn Tyr Asn
    130                 135                 140

Ser Gln Asn Val Tyr Ile Met Ala Asp Lys Gln Lys Asn Gly Ile Lys
145                 150                 155                 160

Val Asn Phe Lys Ile Arg His Asn Ile Glu Asp Gly Ser Val Gln Leu
                165                 170                 175

Ala Asp His Tyr Gln Gln Asn Thr Pro Ile Gly Asp Gly Pro Val Leu
            180                 185                 190

Leu Pro Asp Asn His Tyr Leu Ser Tyr Gln Ser Ala Leu Ser Lys Asp
        195                 200                 205

Pro Asn Glu Lys Arg Asp His Met Val Leu Leu Glu Phe Val Thr Ala
    210                 215                 220

Ala Gly Ile Thr His Gly Met Asp Glu Leu Tyr Lys Ser Gly Leu Arg
225                 230                 235                 240

Ser Arg Ala Thr Met Glu Val Gln Leu Gly Leu Gly Arg Val Tyr Pro
                245                 250                 255

Arg Pro Pro Ser Lys Thr Tyr Arg Gly Ala Phe Gln Asn Leu Phe Gln
            260                 265                 270

Ser Val Arg Glu Val Ile Gln Asn Pro Gly Pro Arg His Pro Glu Ala
        275                 280                 285

Ala Ser Ala Ala Pro Pro Gly Ala Ser Leu Leu Leu Leu Gln Gln Gln
    290                 295                 300

Gln Gln Gln Gln Gln Gln Gln Gln Gln Gln Gln Gln Gln Gln Gln Gln
```

```
            305                 310                 315                 320
        Gln Gln Gln Gln Glu Thr Ser Pro Arg Gln Gln Gln Gln Gln Gly
                        325                 330                 335
        Glu Asp Gly Ser Pro Gln Ala His Arg Arg Gly Pro Thr Gly Tyr Leu
                        340                 345                 350
        Val Leu Asp Glu Gln Gln Pro Ser Gln Pro Gln Ser Ala Leu Glu
                        355                 360                 365
        Cys His Pro Glu Arg Gly Cys Val Pro Glu Pro Gly Ala Ala Val Ala
                    370                 375                 380
        Ala Ser Lys Gly Leu Pro Gln Gln Leu Pro Ala Pro Pro Asp Glu Asp
        385                 390                 395                 400
        Asp Ser Ala Ala Pro Ser Thr Leu Ser Leu Leu Gly Pro Thr Phe Pro
                            405                 410                 415
        Gly Leu Ser Ser Cys Ser Ala Asp Leu Lys Asp Ile Leu Ser Glu Ala
                        420                 425                 430
        Ser Thr Met Gln Leu Leu Gln Gln Gln Gln Glu Ala Val Ser Glu
                    435                 440                 445
        Gly Ser Ser Ser Gly Arg Ala Arg Glu Ala Ser Gly Ala Pro Thr Ser
                    450                 455                 460
        Ser Lys Asp Asn Tyr Leu Gly Gly Thr Ser Thr Ile Ser Asp Asn Ala
        465                 470                 475                 480
        Lys Glu Leu Cys Lys Ala Val Ser Val Ser Met Gly Leu Gly Val Glu
                            485                 490                 495
        Ala Leu Glu His Leu Ser Pro Gly Glu Gln Leu Arg Gly Asp Cys Met
                        500                 505                 510
        Tyr Ala Pro Leu Leu Gly Val Pro Pro Ala Val Arg Pro Thr Pro Cys
                    515                 520                 525
        Ala Pro Leu Ala Glu Cys Lys Gly Ser Leu Leu Asp Asp Ser Ala Gly
                    530                 535                 540
        Lys Ser Thr Glu Asp Thr Ala Glu Tyr Ser Pro Phe Lys Gly Gly Tyr
        545                 550                 555                 560
        Thr Lys Gly Leu Glu Gly Glu Ser Leu Gly Cys Ser Gly Ser Ala Ala
                            565                 570                 575
        Ala Gly Ser Ser Gly Thr Leu Glu Leu Pro Ser Thr Leu Ser Leu Tyr
                    580                 585                 590
        Lys Ser Gly Ala Leu Asp Glu Ala Ala Tyr Gln Ser Arg Asp Tyr
                595                 600                 605
        Tyr Asn Phe Pro Leu Ala Leu Ala Gly Pro Pro Pro Pro Pro Pro
            610                 615                 620
        Pro His Pro His Ala Arg Ile Lys Leu Glu Asn Pro Leu Asp Tyr Gly
        625                 630                 635                 640
        Ser Ala Trp Ala Ala Ala Ala Gln Cys Arg Tyr Gly Asp Leu Ala
                        645                 650                 655
        Ser Leu His Gly Ala Gly Ala Ala Gly Pro Gly Ser Gly Ser Pro Ser
                    660                 665                 670
        Ala Ala Ala Ser Ser Ser Trp His Thr Leu Phe Thr Ala Glu Glu Gly
                    675                 680                 685
        Gln Leu Tyr Gly Pro Cys Gly Gly Gly Gly Gly Gly Gly Gly
                690                 695                 700
        Gly Gly Gly Gly Gly Gly Gly Gly Gly Gly Gly Glu Ala Gly
        705                 710                 715                 720
        Ala Val Ala Pro Tyr Gly Tyr Thr Arg Pro Pro Gln Gly Leu Ala Gly
                        725                 730                 735
```

-continued

```
Gln Glu Ser Asp Phe Thr Ala Pro Asp Val Trp Tyr Pro Gly Gly Met
            740                 745                 750

Val Ser Arg Val Pro Tyr Pro Ser Pro Thr Cys Val Lys Ser Glu Met
            755                 760                 765

Gly Pro Trp Met Asp Ser Tyr Ser Gly Pro Tyr Gly Asp Met Arg Leu
    770                 775                 780

Glu Thr Ala Arg Asp His Val Leu Pro Ile Asp Tyr Tyr Phe Pro Pro
785                 790                 795                 800

Gln Lys Thr Cys Leu Ile Cys Gly Asp Glu Ala Ser Gly Cys His Tyr
        805                 810                 815

Gly Ala Leu Thr Cys Gly Ser Cys Lys Val Phe Phe Lys Arg Ala Ala
        820                 825                 830

Glu Gly Lys Gln Lys Tyr Leu Cys Ala Ser Arg Asn Asp Cys Thr Ile
        835                 840                 845

Asp Lys Phe Arg Arg Lys Asn Cys Pro Ser Cys Arg Leu Arg Lys Cys
    850                 855                 860

Tyr Glu Ala Gly Met Thr Leu Gly Ala Arg Lys Leu Lys Lys Leu Gly
865                 870                 875                 880

Asn Leu Lys Leu Gln Glu Glu Gly Glu Ala Ser Ser Thr Thr Ser Pro
            885                 890                 895

Thr Glu Glu Thr Thr Gln Lys Leu Thr Val Ser His Ile Glu Gly Tyr
            900                 905                 910

Glu Cys Gln Pro Ile Phe Leu Asn Val Leu Glu Ala Ile Glu Pro Gly
        915                 920                 925

Val Val Cys Ala Gly His Asp Asn Asn Gln Pro Asp Ser Phe Ala Ala
    930                 935                 940

Leu Leu Ser Ser Leu Asn Glu Leu Gly Glu Arg Gln Leu Val His Met
945                 950                 955                 960

Val Lys Trp Ala Lys Ala Leu Pro Gly Phe Arg Asn Leu His Val Asp
            965                 970                 975

Asp Gln Met Ala Val Ile Gln Tyr Ser Trp Met Gly Leu Met Val Phe
            980                 985                 990

Ala Met Gly Trp Arg Ser Phe Thr  Asn Val Asn Ser Arg  Met Leu Tyr
            995                 1000                1005

Phe Ala  Pro Asp Leu Val Phe  Asn Glu Tyr Arg Met  His Lys Ser
    1010                1015                1020

Arg  Met Tyr Ser Gln Cys Val  Arg Met Arg His Leu  Ser Gln Glu
    1025                1030                1035

Phe Gly  Trp Leu Gln Ile Thr  Pro Gln Glu Phe Leu  Cys Met Lys
    1040                1045                1050

Ala Leu  Leu Leu Phe Ser Ile  Ile Pro Val Asp Gly  Leu Lys Asn
    1055                1060                1065

Gln Lys  Phe Phe Asp Glu Leu  Arg Met Asn Tyr Ile  Lys Glu Leu
    1070                1075                1080

Asp Arg  Ile Ile Ala Cys Lys  Arg Lys Asn Pro Thr  Ser Cys Ser
    1085                1090                1095

Arg Arg  Phe Tyr Gln Leu Thr  Lys Leu Leu Asp Ser  Val Gln Pro
    1100                1105                1110

Ile Ala  Arg Glu Leu His Gln  Phe Thr Phe Asp Leu  Leu Ile Lys
    1115                1120                1125

Ser His  Met Val Ser Val Asp  Phe Pro Glu Met Met  Ala Glu Ile
    1130                1135                1140
```

```
Ile Ser Val Gln Val Pro Lys Ile Leu Ser Gly Lys Val Lys Pro
    1145                1150                1155
Ile Tyr Phe His Thr Gln Lys Asp Pro Pro Val Ala Thr Met Ser
    1160                1165                1170
Lys Gly Glu Glu Leu Phe Thr Gly Val Val Pro Ile Leu Val Glu
    1175                1180                1185
Leu Asp Gly Asp Val Asn Gly His Lys Phe Ser Val Ser Gly Glu
    1190                1195                1200
Gly Glu Gly Asp Ala Thr Tyr Gly Lys Leu Thr Leu Lys Phe Ile
    1205                1210                1215
Cys Thr Thr Gly Lys Leu Pro Val Pro Trp Pro Thr Leu Val Thr
    1220                1225                1230
Thr Phe Xaa Leu Gln Cys Phe Ala Arg Tyr Pro Asp His Met Lys
    1235                1240                1245
Arg His Asp Phe Phe Lys Ser Ala Met Pro Glu Gly Tyr Val Gln
    1250                1255                1260
Glu Arg Thr Ile Phe Phe Lys Asp Asp Gly Asn Tyr Lys Thr Arg
    1265                1270                1275
Ala Glu Val Lys Phe Glu Gly Asp Thr Leu Val Asn Arg Ile Glu
    1280                1285                1290
Leu Lys Gly Ile Asp Phe Lys Glu Asp Gly Asn Ile Leu Gly His
    1295                1300                1305
Lys Leu Glu Tyr Asn Tyr Asn Ser Gln Asn Val Tyr Ile Met Ala
    1310                1315                1320
Asp Lys Gln Lys Asn Gly Ile Lys Val Asn Phe Lys Ile Arg His
    1325                1330                1335
Asn Ile Glu Asp Gly Ser Val Gln Leu Ala Asp His Tyr Gln Gln
    1340                1345                1350
Asn Thr Pro Ile Gly Asp Gly Pro Val Leu Leu Pro Asp Asn His
    1355                1360                1365
Tyr Leu Ser Tyr Gln Ser Ala Leu Ser Lys Asp Pro Asn Glu Lys
    1370                1375                1380
Arg Asp His Met Val Leu Leu Glu Phe Val Thr Ala Ala Gly Ile
    1385                1390                1395
Thr His Gly Met Asp Glu Leu Tyr Lys
    1400                1405

<210> SEQ ID NO 4
<211> LENGTH: 1407
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of human T877S mutant androgen
      receptor with two yellow fluorescent proteins, one each linked
      at the carboxy and amino termini of the mutant androgen
      sequence
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (1236)..(1236)
<223> OTHER INFORMATION: Any amino acid

<400> SEQUENCE: 4

Met Ser Lys Gly Glu Glu Leu Phe Thr Gly Val Val Pro Ile Leu Val
```

-continued

```
1               5                   10                  15
Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Xaa Leu Gln Cys Phe Ala Arg Tyr Pro Asp His Met Lys Arg His Asp
65                  70                  75                  80

Phe Phe Lys Ser Ala Met Pro Glu Gly Tyr Val Gln Glu Arg Thr Ile
                85                  90                  95

Phe Phe Lys Asp Asp Gly Asn Tyr Lys Thr Arg Ala Glu Val Lys Phe
                100                 105                 110

Glu Gly Asp Thr Leu Val Asn Arg Ile Glu Leu Lys Gly Ile Asp Phe
            115                 120                 125

Lys Glu Asp Gly Asn Ile Leu Gly His Lys Leu Glu Tyr Asn Tyr Asn
        130                 135                 140

Ser Gln Asn Val Tyr Ile Met Ala Asp Lys Gln Lys Asn Gly Ile Lys
145                 150                 155                 160

Val Asn Phe Lys Ile Arg His Asn Ile Glu Asp Gly Ser Val Gln Leu
                165                 170                 175

Ala Asp His Tyr Gln Gln Asn Thr Pro Ile Gly Asp Gly Pro Val Leu
            180                 185                 190

Leu Pro Asp Asn His Tyr Leu Ser Tyr Gln Ser Ala Leu Ser Lys Asp
            195                 200                 205

Pro Asn Glu Lys Arg Asp His Met Val Leu Leu Glu Phe Val Thr Ala
        210                 215                 220

Ala Gly Ile Thr His Gly Met Asp Glu Leu Tyr Lys Ser Gly Leu Arg
225                 230                 235                 240

Ser Arg Ala Thr Met Glu Val Gln Leu Gly Leu Gly Arg Val Tyr Pro
                245                 250                 255

Arg Pro Pro Ser Lys Thr Tyr Arg Gly Ala Phe Gln Asn Leu Phe Gln
            260                 265                 270

Ser Val Arg Glu Val Ile Gln Asn Pro Gly Pro Arg His Pro Glu Ala
        275                 280                 285

Ala Ser Ala Ala Pro Pro Gly Ala Ser Leu Leu Leu Leu Gln Gln Gln
            290                 295                 300

Gln Gln Gln Gln Gln Gln Gln Gln Gln Gln Gln Gln Gln Gln Gln Gln
305                 310                 315                 320

Gln Gln Gln Gln Glu Thr Ser Pro Arg Gln Gln Gln Gln Gln Gln Gly
                325                 330                 335

Glu Asp Gly Ser Pro Gln Ala His Arg Arg Gly Pro Thr Gly Tyr Leu
            340                 345                 350

Val Leu Asp Glu Glu Gln Pro Ser Gln Pro Gln Ser Ala Leu Glu
            355                 360                 365

Cys His Pro Glu Arg Gly Cys Val Pro Glu Pro Gly Ala Ala Val Ala
        370                 375                 380

Ala Ser Lys Gly Leu Pro Gln Gln Leu Pro Ala Pro Pro Asp Glu Asp
385                 390                 395                 400

Asp Ser Ala Ala Pro Ser Thr Leu Ser Leu Leu Gly Pro Thr Phe Pro
                405                 410                 415

Gly Leu Ser Ser Cys Ser Ala Asp Leu Lys Asp Ile Leu Ser Glu Ala
            420                 425                 430
```

```
Ser Thr Met Gln Leu Leu Gln Gln Gln Gln Glu Ala Val Ser Glu
        435                 440                 445
Gly Ser Ser Ser Gly Arg Ala Arg Glu Ala Ser Gly Ala Pro Thr Ser
    450                 455                 460
Ser Lys Asp Asn Tyr Leu Gly Gly Thr Ser Thr Ile Ser Asp Asn Ala
465                 470                 475                 480
Lys Glu Leu Cys Lys Ala Val Ser Val Ser Met Gly Leu Gly Val Glu
                485                 490                 495
Ala Leu Glu His Leu Ser Pro Gly Glu Gln Leu Arg Gly Asp Cys Met
                500                 505                 510
Tyr Ala Pro Leu Leu Gly Val Pro Pro Ala Val Arg Pro Thr Pro Cys
        515                 520                 525
Ala Pro Leu Ala Glu Cys Lys Gly Ser Leu Leu Asp Asp Ser Ala Gly
    530                 535                 540
Lys Ser Thr Glu Asp Thr Ala Glu Tyr Ser Pro Phe Lys Gly Gly Tyr
545                 550                 555                 560
Thr Lys Gly Leu Glu Gly Glu Ser Leu Gly Cys Ser Gly Ser Ala Ala
                565                 570                 575
Ala Gly Ser Ser Gly Thr Leu Glu Leu Pro Ser Thr Leu Ser Leu Tyr
            580                 585                 590
Lys Ser Gly Ala Leu Asp Glu Ala Ala Tyr Gln Ser Arg Asp Tyr
            595                 600                 605
Tyr Asn Phe Pro Leu Ala Leu Ala Gly Pro Pro Pro Pro Pro Pro
610                 615                 620
Pro His Pro His Ala Arg Ile Lys Leu Glu Asn Pro Leu Asp Tyr Gly
625                 630                 635                 640
Ser Ala Trp Ala Ala Ala Ala Gln Cys Arg Tyr Gly Asp Leu Ala
            645                 650                 655
Ser Leu His Gly Ala Gly Ala Ala Gly Pro Gly Ser Gly Ser Pro Ser
            660                 665                 670
Ala Ala Ala Ser Ser Ser Trp His Thr Leu Phe Thr Ala Glu Glu Gly
        675                 680                 685
Gln Leu Tyr Gly Pro Cys Gly Gly Gly Gly Gly Gly Gly Gly Gly
    690                 695                 700
Gly Gly Gly Gly Gly Gly Gly Gly Gly Gly Gly Gly Gly Glu Ala Gly
705                 710                 715                 720
Ala Val Ala Pro Tyr Gly Tyr Thr Arg Pro Pro Gln Gly Leu Ala Gly
                725                 730                 735
Gln Glu Ser Asp Phe Thr Ala Pro Asp Val Trp Tyr Pro Gly Gly Met
            740                 745                 750
Val Ser Arg Val Pro Tyr Pro Ser Pro Thr Cys Val Lys Ser Glu Met
        755                 760                 765
Gly Pro Trp Met Asp Ser Tyr Ser Gly Pro Tyr Gly Asp Met Arg Leu
    770                 775                 780
Glu Thr Ala Arg Asp His Val Leu Pro Ile Asp Tyr Tyr Phe Pro Pro
785                 790                 795                 800
Gln Lys Thr Cys Leu Ile Cys Gly Asp Glu Ala Ser Gly Cys His Tyr
                805                 810                 815
Gly Ala Leu Thr Cys Gly Ser Cys Lys Val Phe Phe Lys Arg Ala Ala
            820                 825                 830
Glu Gly Lys Gln Lys Tyr Leu Cys Ala Ser Arg Asn Asp Cys Thr Ile
        835                 840                 845
```

```
Asp Lys Phe Arg Arg Lys Asn Cys Pro Ser Cys Arg Leu Arg Lys Cys
850                 855                 860

Tyr Glu Ala Gly Met Thr Leu Gly Ala Arg Lys Leu Lys Lys Leu Gly
865                 870                 875                 880

Asn Leu Lys Leu Gln Glu Glu Gly Ala Ser Ser Thr Thr Ser Pro
        885                 890                 895

Thr Glu Glu Thr Thr Gln Lys Leu Thr Val Ser His Ile Glu Gly Tyr
        900                 905                 910

Glu Cys Gln Pro Ile Phe Leu Asn Val Leu Glu Ala Ile Glu Pro Gly
        915                 920                 925

Val Val Cys Ala Gly His Asp Asn Asn Gln Pro Asp Ser Phe Ala Ala
930                 935                 940

Leu Leu Ser Ser Leu Asn Glu Leu Gly Glu Arg Gln Leu Val His Val
945                 950                 955                 960

Val Lys Trp Ala Lys Ala Leu Pro Gly Phe Arg Asn Leu His Val Asp
                965                 970                 975

Asp Gln Met Ala Val Ile Gln Tyr Ser Trp Met Gly Leu Met Val Phe
        980                 985                 990

Ala Met Gly Trp Arg Ser Phe Thr Asn Val Asn Ser Arg Met Leu Tyr
        995                 1000                1005

Phe Ala Pro Asp Leu Val Phe Asn Glu Tyr Arg Met His Lys Ser
    1010                1015                1020

Arg Met Tyr Ser Gln Cys Val Arg Met Arg His Leu Ser Gln Glu
    1025                1030                1035

Phe Gly Trp Leu Gln Ile Thr Pro Gln Glu Phe Leu Cys Met Lys
    1040                1045                1050

Ala Leu Leu Leu Phe Ser Ile Ile Pro Val Asp Gly Leu Lys Asn
    1055                1060                1065

Gln Lys Phe Phe Asp Glu Leu Arg Met Asn Tyr Ile Lys Glu Leu
    1070                1075                1080

Asp Arg Ile Ile Ala Cys Lys Arg Lys Asn Pro Thr Ser Cys Ser
    1085                1090                1095

Arg Arg Phe Tyr Gln Leu Thr Lys Leu Leu Asp Ser Val Gln Pro
    1100                1105                1110

Ile Ala Arg Glu Leu His Gln Phe Ser Phe Asp Leu Leu Ile Lys
    1115                1120                1125

Ser His Met Val Ser Val Asp Phe Pro Glu Met Met Ala Glu Ile
    1130                1135                1140

Ile Ser Val Gln Val Pro Lys Ile Leu Ser Gly Lys Val Lys Pro
    1145                1150                1155

Ile Tyr Phe His Thr Gln Lys Asp Pro Pro Val Ala Thr Met Ser
    1160                1165                1170

Lys Gly Glu Glu Leu Phe Thr Gly Val Val Pro Ile Leu Val Glu
    1175                1180                1185

Leu Asp Gly Asp Val Asn Gly His Lys Phe Ser Val Ser Gly Glu
    1190                1195                1200

Gly Glu Gly Asp Ala Thr Tyr Gly Lys Leu Thr Leu Lys Phe Ile
    1205                1210                1215

Cys Thr Thr Gly Lys Leu Pro Val Pro Trp Pro Thr Leu Val Thr
    1220                1225                1230

Thr Phe Xaa Leu Gln Cys Phe Ala Arg Tyr Pro Asp His Met Lys
    1235                1240                1245

Arg His Asp Phe Phe Lys Ser Ala Met Pro Glu Gly Tyr Val Gln
```

-continued

```
                      1250                1255                1260

Glu Arg Thr Ile Phe Phe Lys Asp Asp Gly Asn Tyr Lys Thr Arg
        1265                1270                1275

Ala Glu Val Lys Phe Glu Gly Asp Thr Leu Val Asn Arg Ile Glu
    1280                1285                1290

Leu Lys Gly Ile Asp Phe Lys Glu Asp Gly Asn Ile Leu Gly His
    1295                1300                1305

Lys Leu Glu Tyr Asn Tyr Asn Ser Gln Asn Val Tyr Ile Met Ala
    1310                1315                1320

Asp Lys Gln Lys Asn Gly Ile Lys Val Asn Phe Lys Ile Arg His
    1325                1330                1335

Asn Ile Glu Asp Gly Ser Val Gln Leu Ala Asp His Tyr Gln Gln
    1340                1345                1350

Asn Thr Pro Ile Gly Asp Gly Pro Val Leu Leu Pro Asp Asn His
    1355                1360                1365

Tyr Leu Ser Tyr Gln Ser Ala Leu Ser Lys Asp Pro Asn Glu Lys
    1370                1375                1380

Arg Asp His Met Val Leu Leu Glu Phe Val Thr Ala Ala Gly Ile
    1385                1390                1395

Thr His Gly Met Asp Glu Leu Tyr Lys
    1400                1405

<210> SEQ ID NO 5
<211> LENGTH: 1407
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fusion protein of human T877A mutant androgen
      receptor with two yellow fluorescent proteins, one each linked at
      the carboxy and amino termini of the mutant androgen
      sequence
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (1236)..(1236)
<223> OTHER INFORMATION: Any amino acid

<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Xaa Leu Gln Cys Phe Ala Arg Tyr Pro Asp His Met Lys Arg His Asp
65                  70                  75                  80

Phe Phe Lys Ser Ala Met Pro Glu Gly Tyr Val Gln Glu Arg Thr Ile
                85                  90                  95

Phe Phe Lys Asp Asp Gly Asn Tyr Lys Thr Arg Ala Glu Val Lys Phe
            100                 105                 110

Glu Gly Asp Thr Leu Val Asn Arg Ile Glu Leu Lys Gly Ile Asp Phe
        115                 120                 125
```

```
Lys Glu Asp Gly Asn Ile Leu Gly His Lys Leu Glu Tyr Asn Tyr Asn
130                 135                 140
Ser Gln Asn Val Tyr Ile Met Ala Asp Lys Gln Lys Asn Gly Ile Lys
145                 150                 155                 160
Val Asn Phe Lys Ile Arg His Asn Ile Glu Asp Gly Ser Val Gln Leu
                165                 170                 175
Ala Asp His Tyr Gln Gln Asn Thr Pro Ile Gly Asp Gly Pro Val Leu
            180                 185                 190
Leu Pro Asp Asn His Tyr Leu Ser Tyr Gln Ser Ala Leu Ser Lys Asp
        195                 200                 205
Pro Asn Glu Lys Arg Asp His Met Val Leu Leu Glu Phe Val Thr Ala
210                 215                 220
Ala Gly Ile Thr His Gly Met Asp Glu Leu Tyr Lys Ser Gly Leu Arg
225                 230                 235                 240
Ser Arg Ala Thr Met Glu Val Gln Leu Gly Leu Gly Arg Val Tyr Pro
                245                 250                 255
Arg Pro Pro Ser Lys Thr Tyr Arg Gly Ala Phe Gln Asn Leu Phe Gln
            260                 265                 270
Ser Val Arg Glu Val Ile Gln Asn Pro Gly Pro Arg His Pro Glu Ala
        275                 280                 285
Ala Ser Ala Ala Pro Pro Gly Ala Ser Leu Leu Leu Leu Gln Gln Gln
290                 295                 300
Gln Gln Gln Gln Gln Gln Gln Gln Gln Gln Gln Gln Gln Gln Gln Gln
305                 310                 315                 320
Gln Gln Gln Gln Glu Thr Ser Pro Arg Gln Gln Gln Gln Gln Gln Gly
                325                 330                 335
Glu Asp Gly Ser Pro Gln Ala His Arg Arg Gly Pro Thr Gly Tyr Leu
            340                 345                 350
Val Leu Asp Glu Glu Gln Gln Pro Ser Gln Pro Gln Ser Ala Leu Glu
        355                 360                 365
Cys His Pro Glu Arg Gly Cys Val Pro Glu Pro Gly Ala Ala Val Ala
370                 375                 380
Ala Ser Lys Gly Leu Pro Gln Gln Leu Pro Ala Pro Pro Asp Glu Asp
385                 390                 395                 400
Asp Ser Ala Ala Pro Ser Thr Leu Ser Leu Leu Gly Pro Thr Phe Pro
                405                 410                 415
Gly Leu Ser Ser Cys Ser Ala Asp Leu Lys Asp Ile Leu Ser Glu Ala
            420                 425                 430
Ser Thr Met Gln Leu Leu Gln Gln Gln Gln Glu Ala Val Ser Glu
        435                 440                 445
Gly Ser Ser Ser Gly Arg Ala Arg Glu Ala Ser Gly Ala Pro Thr Ser
450                 455                 460
Ser Lys Asp Asn Tyr Leu Gly Gly Thr Ser Thr Ile Ser Asp Asn Ala
465                 470                 475                 480
Lys Glu Leu Cys Lys Ala Val Ser Val Ser Met Gly Leu Gly Val Glu
                485                 490                 495
Ala Leu Glu His Leu Ser Pro Gly Glu Gln Leu Arg Gly Asp Cys Met
            500                 505                 510
Tyr Ala Pro Leu Leu Gly Val Pro Pro Ala Val Arg Pro Thr Pro Cys
        515                 520                 525
Ala Pro Leu Ala Glu Cys Lys Gly Ser Leu Leu Asp Asp Ser Ala Gly
530                 535                 540
```

```
Lys Ser Thr Glu Asp Thr Ala Glu Tyr Ser Pro Phe Lys Gly Gly Tyr
545                 550                 555                 560

Thr Lys Gly Leu Glu Gly Glu Ser Leu Gly Cys Ser Gly Ser Ala Ala
            565                 570                 575

Ala Gly Ser Ser Gly Thr Leu Glu Leu Pro Ser Thr Leu Ser Leu Tyr
        580                 585                 590

Lys Ser Gly Ala Leu Asp Glu Ala Ala Tyr Gln Ser Arg Asp Tyr
    595                 600                 605

Tyr Asn Phe Pro Leu Ala Leu Ala Gly Pro Pro Pro Pro Pro Pro
    610                 615                 620

Pro His Pro His Ala Arg Ile Lys Leu Glu Asn Pro Leu Asp Tyr Gly
625                 630                 635                 640

Ser Ala Trp Ala Ala Ala Ala Gln Cys Arg Tyr Gly Asp Leu Ala
            645                 650                 655

Ser Leu His Gly Ala Gly Ala Ala Gly Pro Gly Ser Gly Ser Pro Ser
        660                 665                 670

Ala Ala Ala Ser Ser Ser Trp His Thr Leu Phe Thr Ala Glu Glu Gly
            675                 680                 685

Gln Leu Tyr Gly Pro Cys Gly Gly Gly Gly Gly Gly Gly Gly Gly
    690                 695                 700

Gly Gly Gly Gly Gly Gly Gly Gly Gly Gly Gly Gly Glu Ala Gly
705                 710                 715                 720

Ala Val Ala Pro Tyr Gly Tyr Thr Arg Pro Pro Gln Gly Leu Ala Gly
                725                 730                 735

Gln Glu Ser Asp Phe Thr Ala Pro Asp Val Trp Tyr Pro Gly Gly Met
            740                 745                 750

Val Ser Arg Val Pro Tyr Pro Ser Pro Thr Cys Val Lys Ser Glu Met
            755                 760                 765

Gly Pro Trp Met Asp Ser Tyr Ser Gly Pro Tyr Gly Asp Met Arg Leu
            770                 775                 780

Glu Thr Ala Arg Asp His Val Leu Pro Ile Asp Tyr Tyr Phe Pro Pro
785                 790                 795                 800

Gln Lys Thr Cys Leu Ile Cys Gly Asp Glu Ala Ser Gly Cys His Tyr
            805                 810                 815

Gly Ala Leu Thr Cys Gly Ser Cys Lys Val Phe Phe Lys Arg Ala Ala
            820                 825                 830

Glu Gly Lys Gln Lys Tyr Leu Cys Ala Ser Arg Asn Asp Cys Thr Ile
            835                 840                 845

Asp Lys Phe Arg Arg Lys Asn Cys Pro Ser Cys Arg Leu Arg Lys Cys
850                 855                 860

Tyr Glu Ala Gly Met Thr Leu Gly Ala Arg Lys Leu Lys Lys Leu Gly
865                 870                 875                 880

Asn Leu Lys Leu Gln Glu Gly Glu Ala Ser Ser Thr Thr Ser Pro
            885                 890                 895

Thr Glu Glu Thr Thr Gln Lys Leu Thr Val Ser His Ile Glu Gly Tyr
            900                 905                 910

Glu Cys Gln Pro Ile Phe Leu Asn Val Leu Glu Ala Ile Glu Pro Gly
            915                 920                 925

Val Val Cys Ala Gly His Asp Asn Asn Gln Pro Asp Ser Phe Ala Ala
            930                 935                 940

Leu Leu Ser Ser Leu Asn Glu Leu Gly Glu Arg Gln Leu Val His Val
945                 950                 955                 960

Val Lys Trp Ala Lys Ala Leu Pro Gly Phe Arg Asn Leu His Val Asp
```

-continued

```
                965                 970                 975
Asp Gln Met Ala Val Ile Gln Tyr Ser Trp Met Gly Leu Met Val Phe
            980                 985                 990
Ala Met Gly Trp Arg Ser Phe Thr Asn Val Asn Ser Arg Met Leu Tyr
        995                1000                1005
Phe Ala Pro Asp Leu Val Phe Asn Glu Tyr Arg Met His Lys Ser
   1010                1015                1020
Arg Met Tyr Ser Gln Cys Val Arg Met Arg His Leu Ser Gln Glu
   1025                1030                1035
Phe Gly Trp Leu Gln Ile Thr Pro Gln Glu Phe Leu Cys Met Lys
   1040                1045                1050
Ala Leu Leu Leu Phe Ser Ile Ile Pro Val Asp Gly Leu Lys Asn
   1055                1060                1065
Gln Lys Phe Phe Asp Glu Leu Arg Met Asn Tyr Ile Lys Glu Leu
   1070                1075                1080
Asp Arg Ile Ile Ala Cys Lys Arg Lys Asn Pro Thr Ser Cys Ser
   1085                1090                1095
Arg Arg Phe Tyr Gln Leu Thr Lys Leu Leu Asp Ser Val Gln Pro
   1100                1105                1110
Ile Ala Arg Glu Leu His Gln Phe Ala Phe Asp Leu Leu Ile Lys
   1115                1120                1125
Ser His Met Val Ser Val Asp Phe Pro Glu Met Met Ala Glu Ile
   1130                1135                1140
Ile Ser Val Gln Val Pro Lys Ile Leu Ser Gly Lys Val Lys Pro
   1145                1150                1155
Ile Tyr Phe His Thr Gln Lys Asp Pro Pro Val Ala Thr Met Ser
   1160                1165                1170
Lys Gly Glu Glu Leu Phe Thr Gly Val Val Pro Ile Leu Val Glu
   1175                1180                1185
Leu Asp Gly Asp Val Asn Gly His Lys Phe Ser Val Ser Gly Glu
   1190                1195                1200
Gly Glu Gly Asp Ala Thr Tyr Gly Lys Leu Thr Leu Lys Phe Ile
   1205                1210                1215
Cys Thr Thr Gly Lys Leu Pro Val Pro Trp Pro Thr Leu Val Thr
   1220                1225                1230
Thr Phe Xaa Leu Gln Cys Phe Ala Arg Tyr Pro Asp His Met Lys
   1235                1240                1245
Arg His Asp Phe Phe Lys Ser Ala Met Pro Glu Gly Tyr Val Gln
   1250                1255                1260
Glu Arg Thr Ile Phe Phe Lys Asp Asp Gly Asn Tyr Lys Thr Arg
   1265                1270                1275
Ala Glu Val Lys Phe Glu Gly Asp Thr Leu Val Asn Arg Ile Glu
   1280                1285                1290
Leu Lys Gly Ile Asp Phe Lys Glu Asp Gly Asn Ile Leu Gly His
   1295                1300                1305
Lys Leu Glu Tyr Asn Tyr Asn Ser Gln Asn Val Tyr Ile Met Ala
   1310                1315                1320
Asp Lys Gln Lys Asn Gly Ile Lys Val Asn Phe Lys Ile Arg His
   1325                1330                1335
Asn Ile Glu Asp Gly Ser Val Gln Leu Ala Asp His Tyr Gln Gln
   1340                1345                1350
Asn Thr Pro Ile Gly Asp Gly Pro Val Leu Leu Pro Asp Asn His
   1355                1360                1365
```

| Tyr | Leu | Ser | Tyr | Gln | Ser | Ala | Leu | Ser | Lys | Asp | Pro | Asn | Glu | Lys |
| | 1370 | | | | 1375 | | | | | 1380 | | | | |

| Arg | Asp | His | Met | Val | Leu | Leu | Glu | Phe | Val | Thr | Ala | Ala | Gly | Ile |
| | 1385 | | | | | 1390 | | | | | 1395 | | | |

| Thr | His | Gly | Met | Asp | Glu | Leu | Tyr | Lys |
| | 1400 | | | | | 1405 | | |

<210> SEQ ID NO 6
<211> LENGTH: 4239
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid coding for fusion protein of human V715M mutant androgen receptor with two yellow fluorescent proteins, one each linked at the carboxy and amino termini of the mutant androgen sequence

<400> SEQUENCE: 6

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagtcc     720
ggactcagat ctcgagccac catggaagtg cagttagggc tgggaagggt ctaccctcgg     780
ccgccgtcca agacctaccg aggagctttc cagaatctgt tccagagcgt gcgcgaagtg     840
atccagaacc cgggccccag cacccagag gccgcgagcg cagcacctcc cggcgccagt     900
ttgctgctgc tgcagcagca gcagcagcag cagcagcagc agcagcagca gcagcagcag     960
cagcagcagc agcagcagca agagactagc cccaggcagc agcagcagca gcagggtgag    1020
gatggttctc cccaagccca tcgtagaggc cccacaggct acctggtcct ggatgaggaa    1080
cagcaacctt cacagccgca gtcggccctg gagtgccacc ccgagagagg ttgcgtccca    1140
gagcctggag ccgccgtggc cgccagcaag gggctgccgc agcagctgcc agcacctccg    1200
gacgaggatg actcagctgc ccatccacg ttgtccctgc tgggcccac tttccccggc    1260
ttaagcagct gctccgctga ccttaaagac atcctgagcg aggccagcac catgcaactc    1320
cttcagcaac agcagcagga agcagtatcc gaaggcagca gcagcgggag agcgagggag    1380
gcctcggggg ctcccacttc ctccaaggac aattacttag ggggcacttc gaccatttct    1440
gacaacgcca aggagttgtg taaggcagtg tcggtgtcca tgggcctggg tgtggaggcg    1500
ttggagcatc tgagtccagg ggaacagctt cgggggggatt gcatgtacgc cccacttttg    1560
ggagttccac ccgctgtgcg tcccactcct tgtgcccat tggccgaatg caaaggttct    1620
```

-continued

```
ctgctagacg acagcgcagg caagagcact gaagatactg ctgagtattc ccctttcaag    1680
ggaggttaca ccaaagggct agaaggcgag agcctaggct gctctggcag cgctgcagca    1740
gggagctccg ggacacttga actgccgtct accctgtctc tctacaagtc cggagcactg    1800
gacgaggcag ctgcgtacca gagtcgcgac tactacaact ttccactggc tctggccgga    1860
ccgccgcccc ctccgccgcc tccccatccc cacgctcgca tcaagctgga aacccgctg     1920
gactacggca gcgcctgggc ggctgcgcg gcgcagtgcc gctatgggga cctggcgagc     1980
ctgcatggcg cgggtgcagc gggacccggt tctgggtcac cctcagccgc cgcttcctca    2040
tcctggcaca ctctcttcac agccgaagaa ggccagttgt atggaccgtg tggtggtggt    2100
gggggtggtg gcggcggcgg cggcggcggc ggcggcggcg gcggcggcgg cggcggcggc    2160
gaggcgggag ctgtagcccc ctacggctac actcggcccc ctcaggggct ggcgggccag    2220
gaaagcgact tcaccgcacc tgatgtgtgg taccctggcg gcatggtgag cagagtgccc    2280
tatcccagtc ccacttgtgt caaaagcgaa atgggcccct ggatggatag ctactccgga    2340
ccttacgggg acatgcgttt ggagactgcc agggaccatg ttttgcccat tgactattac    2400
tttccacccc agaagacctg cctgatctgt ggagatgaag cttctgggtg tcactatgga    2460
gctctcacat gtggaagctg caaggtcttc ttcaaaagag ccgctgaagg gaaacagaag    2520
tacctgtgcg ccagcagaaa tgattgcact attgataaat tccgaaggaa aaattgtcca    2580
tcttgtcgtc ttcggaaatg ttatgaagca gggatgactc tgggagcccg gaagctgaag    2640
aaacttggta atctgaaact acaggaggaa ggagaggctt ccagcaccac cagccccact    2700
gaggagacaa cccagaagct gacagtgtca cacattgaag ctatgaatg tcagcccatc     2760
tttctgaatg tcctggaagc cattgagcca ggtgtagtgt gtgctggaca cgacaacaac    2820
cagcccgact cctttgcagc cttgctctct agcctcaatg aactgggaga gagacagctt    2880
gtacacatgg tcaagtgggc caaggccttg cctggcttcc gcaacttaca cgtgacgac     2940
cagatggctg tcattcagta ctcctggatg gggctcatgg tgtttgccat gggctggcga    3000
tccttcacca atgtcaactc caggatgctc tacttcgccc ctgatctggt tttcaatgag    3060
taccgcatgc acaagtcccg gatgtacagc cagtgtgtcc gaatgaggca cctctctcaa    3120
gagtttggat ggctccaaat cacccccag gaattcctgt gcatgaaagc actgctactc     3180
ttcagcatta ttccagtgga tgggctgaaa aatcaaaaat tctttgatga acttcgaatg    3240
aactacatca aggaactcga tcgtatcatt gcatgcaaaa gaaaaaatcc cacatcctgc    3300
tcaagacgct tctaccagct caccaagctc ctggactccg tgcagcctat tgcgagagag    3360
ctgcatcagt tcacttttga cctgctaatc aagtcacaca tggtgagcgt ggactttccg    3420
gaaatgatgg cagagatcat ctctgtgcaa gtgcccaaga tcctttctgg aaagtcaag     3480
cccatctatt tccacacccca gaaggatcca ccggtcgcca ccatggtgag caagggcgag    3540
gagctgttca ccggggtggt gcccatcctg gtcgagctgg acggcgacgt aaacggccac    3600
aagttcagcg tgtccggcga gggcgagggc gatgccacct acggcaagct gaccctgaag    3660
ttcatctgca ccaccggcaa gctgcccgtg cctggcccca cctcgtgac cacccttcggc    3720
tacggcctgc agtgcttcgc ccgctacccc gaccacatga agcagcacga cttcttcaag    3780
tccgccatgc ccgaaggcta cgtccaggag cgcaccatct tcttcaagga cgacggcaac    3840
tacaagaccc gcgccgaggt gaagttcgag ggcgacaccc tggtgaaccg catcgagctg    3900
aagggcatcg acttcaagga ggacggcaac atcctggggc acaagctgga gtacaactac    3960
```

| | |
|---|---|
| aacagccaca acgtctatat catggccgac aagcagaaga acggcatcaa ggtgaacttc | 4020 |
| aagatccgcc acaacatcga ggacggcagc gtgcagctcg ccgaccacta ccagcagaac | 4080 |
| accccatcg gcgacggccc cgtgctgctg cccgacaacc actacctgag ctaccagtcc | 4140 |
| gccctgagca agacccccaa cgagaagcgc gatcacatgg tcctgctgga gttcgtgacc | 4200 |
| gccgccggga tcactctcgg catggacgag ctgtacaag | 4239 |

<210> SEQ ID NO 7
<211> LENGTH: 4239
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Nucleic acid coding for fusion protein of human
T877S mutant androgen receptor with two yellow fluorescent
proteins, one each linked at the carboxy and amino termini of the
mutant androgen sequence

<400> SEQUENCE: 7

| | |
|---|---|
| atggtgagca agggcgagga gctgttcacc ggggtggtgc ccatcctggt cgagctggac | 60 |
| ggcgacgtaa acgccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtcc | 720 |
| ggactcagat ctcgagccac catggaagtg cagttagggc tgggaagggt ctaccctcgg | 780 |
| ccgccgtcca agacctaccg aggagctttc cagaatctgt tccagagcgt gcgcgaagtg | 840 |
| atccagaacc cgggccccag gcacccagag gccgcgagcg cagcacctcc cggcgccagt | 900 |
| ttgctgctgc tgcagcagca gcagcagcag cagcagcagc agcagcagca gcagcagcag | 960 |
| cagcagcagc agcagcagca agagactagc cccaggcagc agcagcagca gcagggtgag | 1020 |
| gatggttctc cccaagccca tcgtagaggc cccacaggct acctggtcct ggatgaggaa | 1080 |
| cagcaacctt cacagccgca gtcggccctg gagtgccacc ccgagagagg ttgcgtccca | 1140 |
| gagcctggag ccgccgtggc cgccagcaag gggctgccgc agcagctgcc agcacctccg | 1200 |
| gacgaggatg actcagctgc ccatccacg ttgtccctgc tgggcccac tttccccggc | 1260 |
| ttaagcagct gctccgctga ccttaaagac atcctgagcg aggccagcac catgcaactc | 1320 |
| cttcagcaac agcagcagga agcagtatcc gaaggcagca gcagcgggag agcgagggag | 1380 |
| gcctcggggg ctcccacttc ctccaaggac aattacttag ggggcacttc gaccatttct | 1440 |
| gacaacgcca aggagttgtg taaggcagtg tcggtgtcca tgggcctggg tgtggaggcg | 1500 |
| ttggagcatc tgagtccagg ggaacagctt cgggggatt gcatgtacgc ccacttttg | 1560 |
| ggagttccac ccgctgtgcg tcccactcct gtgcccccat ggccgaatg caaaggttct | 1620 |

```
ctgctagacg acagcgcagg caagagcact gaagatactg ctgagtattc ccctttcaag    1680
ggaggttaca ccaaagggct agaaggcgag agcctaggct gctctggcag cgctgcagca    1740
gggagctccg ggacacttga actgccgtct accctgtctc tctacaagtc cggagcactg    1800
gacgaggcag ctgcgtacca gagtcgcgac tactacaact ttccactggc tctggccgga    1860
ccgccgcccc ctccgccgcc tccccatccc cacgctcgca tcaagctgga aacccgctg     1920
gactacggca gcgcctgggc ggctgcggcg gcgcagtgcc gctatgggga cctggcgagc    1980
ctgcatggcg cgggtgcagc gggacccggt tctgggtcac cctcagccgc gcttcctca     2040
tcctggcaca ctctcttcac agccgaagaa ggccagttgt atggaccgtg tggtggtggt    2100
gggggtggtg gcggcggcgg cggcggcggc ggcggcggcg gcggcggcgg cggcggcggc    2160
gaggcgggag ctgtagcccc ctacggctac actcggcccc tcaggggct ggcgggccag     2220
gaaagcgact tcaccgcacc tgatgtgtgg taccctggcg gcatggtgag cagagtgccc    2280
tatcccagtc ccacttgtgt caaaagcgaa atgggcccct ggatggatag ctactccgga    2340
ccttacgggg acatgcgttt ggagactgcc agggaccatg ttttgcccat tgactattac    2400
tttccacccc agaagacctg cctgatctgt ggagatgaag cttctgggtg tcactatgga    2460
gctctcacat gtggaagctg caaggtcttc ttcaaaagag ccgctgaagg gaaacagaag    2520
tacctgtgcg ccagcagaaa tgattgcact attgataaat ccgaaggaa aaattgtcca     2580
tcttgtcgtc ttcggaaatg ttatgaagca gggatgactc tgggagcccg aagctgaag     2640
aaacttggta atctgaaact acaggaggaa ggagaggctt ccagcaccac cagccccact    2700
gaggagacaa cccagaagct gacagtgtca cacattgaag ctatgaatg tcagcccatc     2760
tttctgaatg tcctggaagc cattgagcca ggtgtagtgt gtgctggaca cgacaacaac    2820
cagcccgact cctttgcagc cttgctctct agcctcaatg aactgggaga gagacagctt    2880
gtacacgtgg tcaagtgggc caaggccttg cctggcttcc gcaacttaca cgtgacgac     2940
cagatggctg tcattcagta ctcctggatg gggctcatgg tgtttgccat gggctggcga    3000
tccttcacca atgtcaactc caggatgctc tacttcgccc ctgatctggt tttcaatgag    3060
taccgcatgc acaagtcccg gatgtacagc cagtgtgtcc gaatgaggca cctctctcaa    3120
gagtttggat ggctccaaat cacccccccag gaattcctgt gcatgaaagc actgctactc    3180
ttcagcatta ttccagtgga tgggctgaaa aatcaaaaat tctttgatga acttcgaatg    3240
aactacatca ggaactcga tcgtatcatt gcatgcaaaa gaaaaaatcc cacatcctgc    3300
tcaagacgct ctaccagct caccaagctc ctggactccg tgcagcctat tgcgagagag   3360
ctgcatcagt tcagctttga cctgctaatc aagtcacaca tggtgagcgt ggactttccg    3420
gaaatgatgg cagagatcat ctctgtgcaa gtgcccaaga tcctttctgg aaagtcaag     3480
cccatctatt tccacaccca gaaggatcca ccggtcgcca ccatggtgag caagggcgag    3540
gagctgttca ccggggtggt gcccatcctg gtcgagctgg acggcgacgt aaacggccac    3600
aagttcagcg tgtccggcga gggcgagggc gatgccacct acggcaagct gaccctgaag    3660
ttcatctgca ccaccggcaa gctgcccgtg cctggcca cctcgtgac caccttcggc      3720
tacggcctgc agtgcttcgc ccgctacccc gaccacatga agcagcacga cttcttcaag    3780
tccgccatgc ccgaaggcta cgtccaggag cgcaccatct tcttcaagga cgacggcaac    3840
tacaagaccc gcgccgaggt gaagttcgag ggcgacaccc tggtgaaccg catcgagctg    3900
aagggcatcg acttcaagga ggacggcaac atcctggggc acaagctgga gtacaactac    3960
```

| | |
|---|---|
| aacagccaca acgtctatat catggccgac aagcagaaga acggcatcaa ggtgaacttc | 4020 |
| aagatccgcc acaacatcga ggacggcagc gtgcagctcg ccgaccacta ccagcagaac | 4080 |
| acccccatcg gcgacggccc cgtgctgctg cccgacaacc actacctgag ctaccagtcc | 4140 |
| gccctgagca agacccccaa cgagaagcgc gatcacatgg tcctgctgga gttcgtgacc | 4200 |
| gccgccggga tcactctcgg catggacgag ctgtacaag | 4239 |

<210> SEQ ID NO 8
<211> LENGTH: 4239
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid coding for fusion protein of human
      T877A mutant androgen receptor with two yellow fluorescent
      proteins, one each linked at the carboxy and amino termini of the
      mutant androgen sequence

<400> SEQUENCE: 8

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtcc | 720 |
| ggactcagat ctcgagccac catggaagtg cagttagggc tgggaagggt ctaccctcgg | 780 |
| ccgccgtcca agacctaccg aggagctttc cagaatctgt tccagagcgt gcgcgaagtg | 840 |
| atccagaacc cgggccccag gcacccagag gccgcgagcg cagcacctcc cggcgccagt | 900 |
| ttgctgctgc tgcagcagca gcagcagcag cagcagcagc agcagcagca gcagcagcag | 960 |
| cagcagcagc agcagcagca agagactagc cccaggcagc agcagcagca gggtgag | 1020 |
| gatggttctc cccaagccca tcgtagaggc cccacaggct acctggtcct ggatgaggaa | 1080 |
| cagcaacctt cacagccgca gtcggccctg gagtgccacc ccgagagagg ttgcgtccca | 1140 |
| gagcctggag ccgccgtggc cgccagcaag gggctgccgc agcagctgcc agcacctccg | 1200 |
| gacgaggatg actcagctgc ccatccacg ttgtccctgc tgggcccac tttccccggc | 1260 |
| ttaagcagct gctccgctga ccttaaagac atcctgagcg aggccagcac catgcaactc | 1320 |
| cttcagcaac agcagcagga agcagtatcc gaaggcagca gcagcgggag agcgagggag | 1380 |
| gcctcggggg ctcccacttc ctccaaggac aattacttag ggggcacttc gaccatttct | 1440 |
| gacaacgcca aggagttgtg taaggcagtg tcggtgtcca tgggcctggg tgtggaggcg | 1500 |
| ttggagcatc tgagtccagg ggaacagctt cgggggatt gcatgtacgc ccactttttg | 1560 |
| ggagttccac ccgctgtgcg tcccactcct tgtgccccat ggccgaatg caaaggttct | 1620 |

```
ctgctagacg acagcgcagg caagagcact gaagatactg ctgagtattc ccctttcaag   1680
ggaggttaca ccaaagggct agaaggcgag agcctaggct gctctggcag cgctgcagca   1740
gggagctccg ggacacttga actgccgtct accctgtctc tctacaagtc cggagcactg   1800
gacgaggcag ctgcgtacca gagtcgcgac tactacaact ttccactggc tctggccgga   1860
ccgccgcccc ctccgccgcc tccccatccc cacgctcgca tcaagctgga aacccgctg    1920 gactacggca cgcctgggc ggctgcggcg gcgcagtgcc gctatgggga cctggcgagc    1980
ctgcatggcg cgggtgcagc gggacccggt tctgggtcac cctcagccgc cgcttcctca   2040
tcctggcaca ctctcttcac agccgaagaa ggccagttgt atggaccgtg tggtggtggt   2100
gggggtggtg gcggcggcgg cggcggcggc ggcggcggcg gcggcggcgg cggcggcggc   2160
gaggcgggag ctgtagcccc ctacggctac actcggcccc ctcaggggct ggcgggccag   2220
gaaagcgact tcaccgcacc tgatgtgtgg taccctggcg gcatggtgag cagagtgccc   2280
tatcccagtc ccacttgtgt caaaagcgaa atgggcccct ggatggatag ctactccgga   2340
ccttacgggg acatgcgttt ggagactgcc agggaccatg ttttgcccat tgactattac   2400
tttccacccc agaagacctg cctgatctgt ggagatgaag cttctgggtg tcactatgga   2460
gctctcacat gtggaagctg caaggtcttc ttcaaaagag ccgctgaagg gaaacagaag   2520
tacctgtgcg ccagcagaaa tgattgcact attgataaat ccgaaggaa aaattgtcca    2580 tcttgtcgtc ttcggaaatg ttatgaagca gggatgactc tgggagcccg gaagctgaag   2640
aaacttggta atctgaaact acaggaggaa ggagaggctt ccagcaccac cagccccact   2700
gaggagacaa cccagaagct gacagtgtca cacattgaag gctatgaatg tcagcccatc   2760
tttctgaatg tcctggaagc cattgagcca ggtgtagtgt gtgctggaca cgacaacaac   2820
cagcccgact cctttgcagc cttgctctct agcctcaatg aactgggaga gagacagctt   2880
gtacacgtgg tcaagtgggc caaggccttg cctggcttcc gcaacttaca cgtggacgac   2940
cagatggctg tcattcagta ctcctggatg gggctcatgg tgtttgccat gggctggcga   3000
tccttcacca atgtcaactc caggatgctc tacttcgccc ctgatctggt tttcaatgag   3060
taccgcatgc acaagtcccg gatgtacagc cagtgtgtcc gaatgaggca cctctctcaa   3120
gagtttggat ggctccaaat cacccccag gaattcctgt gcatgaaagc actgctactc   3180
ttcagcatta ttccagtgga tgggctgaaa aatcaaaaat tctttgatga acttcgaatg   3240
aactacatca aggaactcga tcgtatcatt gcatgcaaaa gaaaaaatcc cacatcctgc   3300
tcaagacgct tctaccagct caccaagctc ctggactccg tgcagcctat tgcgagagag   3360
ctgcatcagt tcgcgtttga cctgctaatc aagtcacaca tggtgagcgt ggactttccg   3420
gaaatgatgg cagagatcat ctctgtgcaa gtgcccaaga tcctttctgg aaagtcaag    3480 cccatctatt tccacaccca gaaggatcca ccggtcgcca ccatggtgag caagggcgag   3540
gagctgttca ccggggtggt gcccatcctg gtcgagctgg acggcgacgt aaacggccac   3600
aagttcagcg tgtccggcga gggcgagggc gatgccacct acggcaagct gaccctgaag   3660
ttcatctgca ccaccggcaa gctgcccgtg ccctggccca ccctcgtgac caccttcggc   3720
tacggcctgc agtgcttcgc ccgctacccc gaccacatga agcagcacga cttcttcaag   3780
tccgccatgc ccgaaggcta cgtccaggag cgcaccatct tcttcaagga cgacggcaac   3840
tacaagaccc gcgccgaggt gaagttcgag ggcgacaccc tggtgaaccg catcgagctg   3900
aagggcatcg acttcaagga ggacggcaac atcctggggc acaagctgga gtacaactac   3960
```

```
aacagccaca acgtctatat catggccgac aagcagaaga acggcatcaa ggtgaacttc    4020
aagatccgcc acaacatcga ggacggcagc gtgcagctcg ccgaccacta ccagcagaac    4080 accccatcg gcgacggccc cgtgctgctg cccgacaacc actacctgag ctaccagtcc    4140
gccctgagca agacccccaa cgagaagcgc gatcacatgg tcctgctgga gttcgtgacc    4200
gccgccggga tcactctcgg catggacgag ctgtacaag                           4239

<210> SEQ ID NO 9
<211> LENGTH: 15
<212> TYPE: DNA
<213> ORGANISM: Homo sapiens
<220> FEATURE:
<223> OTHER INFORMATION: Androgen receptor-binding promoter element
<220> FEATURE:
<221> NAME/KEY: modified_base
<222> LOCATION: (7)..(9)
<223> OTHER INFORMATION: a, c, t, g, unknown or other

<400> SEQUENCE: 9
agaacannnt gttct                                                     15
```

ULTRASENSITIVE ANDROGEN RECEPTOR BIOASSAY

CROSS-REFERENCE TO RELATED APPLICATIONS

This application claims priority to International Application No. PCT/US2015/022301, entitled "Ultrasensitive Androgen Receptor Bioassay," filed on Mar. 24, 2015, which claims priority to U.S. Provisional Application No. 61/970,883, entitled "Ultrasensitive Androgen Receptor Bioassay," filed on Mar. 26, 2014, each of which is incorporated by reference herein in its entirety.

REFERENCE TO SEQUENCE LISTING, A TABLE, OR A COMPUTER PROGRAM LISTING COMPACT DISK APPENDIX

This application is submitted with a computer readable sequence listing, submitted herewith via EFS as the ASCII text file named: "UCSF009PCT_SL.txt", file size approximately 56,792 bytes, created on Mar. 23, 2015 and hereby incorporated by reference in its entirety.

STATEMENT REGARDING FEDERALLY SPONSORED RESEARCH OR DEVELOPMENT

Not Applicable.

BACKGROUND OF THE INVENTION

Androgens are important in regulating various aspects of human physiology and are the principal male sex hormone. These hormones exert their biological influence via the androgen receptor (AR). The androgen receptor binds androgens in the cytoplasm, and upon binding of the target ligand, the receptor is translocated to the nucleus. There, DNA binding motifs present on the androgen receptor bind complementary sequences of various genes and promote their expression. The human AR gene is mapped to the X chromosome and codes for a protein of 919 amino acids.

Androgens are applied in a therapeutic context for treating hormonal deficiencies. They are also implicated in prostate cancer growth and progression. Additionally, androgens are sometimes used as performance enhancing substances, in contradiction of laws and the rules of athletic regulatory bodies. Accordingly, in each of these and other arenas, there is a need for sensitive androgen detection techniques. Currently-used methods include mass spectrometry analyses for the most predominant androgen, testosterone, which is highly sensitive (to 1 ng/dl). Mass spectrometry for a limited number of androgens other than testosterone also is available but is extremely expensive. Immunoassays specific for the most predominant androgen, testosterone, exist as well, but are of variable accuracy; for example the Endocrine Society recommends that immunoassays not be used for the detection of testosterone levels in normal females.

Drugs that inhibit the synthesis of androgens may be applied in a therapeutic context for treating conditions in which androgens exacerbate the disease, such as prostate cancer. The limitations of measurement of androgen levels in patients undergoing those androgen-lowering therapies include their poor sensitivity at the levels of testosterone present in androgen-suppressed patients. The other concern for testosterone measurement in these patients is that androgens other than testosterone may be contributing to the patient's clinical presentation.

Anti-androgens, drugs that block the activation of the AR by androgens, also are applied in a therapeutic context for treating hormonal excess, often in conjunction with androgen-lowering therapies. No measurement of the levels of those anti-androgens is typically conducted. Measurement of testosterone alone does not provide information about the patient's androgen status when they are being treated with anti-androgens.

The physiologically effective androgen levels also are affected by androgen-specific binding factors present in the serum of patients, including serum sex hormone binding globulins (SHBG's, also called sex steroid binding globulins, SSBG's), and by less androgen-specific binding proteins such as albumin. Serum SHBG's currently must be separately quantified in order to examine whether a patient's unique SHBG levels affect the availability of the measured androgens extracted from serum.

There are existing assays based on the expression of reporter genes linked to androgen-responsive elements, wherein expression of the reporter gene is activated by the presence of androgens bound to wild type AR proteins. These AR-based assays provide an inexpensive, facile method of testing for all androgens in biological samples, however their sensitivity is not optimal. Current AR assays based on the wild type receptor do not accurately measure androgens below the physiological threshold, particularly when measuring activity in serum that is diluted when introduced into the measurement medium. Laborious concentration steps may be conducted on androgens extracted from serum, but that eliminates the serum binding factor contributions and may introduce artifacts and inaccuracies through the selective extraction and concentration of specific androgens or anti-androgens or through variations in extraction efficacy.

Accordingly, there is a need in the art for novel assays which improve the ease and economy of current AR assays while greatly increasing the sensitivity of detection.

SUMMARY OF THE INVENTION

Provided herein is a novel assay which enables the sensitive detection of androgens, the detection of a broad spectrum of androgen species, and the detection of other hormones of interest. The assay relies on the use of a sensitive mutant AR combined with a reporter gene and the invention encompasses novel methods of using such constructs to detect androgens.

Described herein are nucleic acid constructs, proteins, cells, assays, and related methods for the detection of androgens at very low concentrations. The tools and methods described herein may also be used in the detection of diverse hormone species. In one embodiment, the invention comprises a nucleic acid sequence coding for one or more sensitive AR mutants linked to one or more nucleic acid constructs coding for a reporter moiety. In one embodiment, the nucleic acid construct is translated into a fusion protein comprising a sensitive mutant AR and one or more reporter moieties. The nucleic acid construct may be introduced into and may be expressed in a reporter cell, where, in the absence of target hormones, the expressed fusion protein of the invention is primarily found in the cytoplasm. The reporter cell may be exposed to a sample putatively containing one or more target hormones. Upon contacting target hormones, the fusion proteins of the invention are translocated to the nucleus, where the concentrated reporter moiety signal may be quantified to determine the presence and amount of target hormone in the sample. A nuclear labeling construct may optionally be used in combination with the reporter construct in order to aid in delineating the nucleus for facile quantification of reporter moiety. This nuclear labeling construct may be utilized generally in a wide range of nuclear translocation assays, including the sensitive AR mutant assays of the invention.

The assays of the invention provide the art with several advantages. In one aspect, the invention provides a tool for the measurement of androgens with greatly increased sensitivity. This allows the use of AR-based assays in low-androgen populations where prior art wild-type AR assays cannot be used. Additionally, the increased sensitivity enables the use of samples that have not been concentrated, which avoids laborious steps and increases accuracy. Also, the assay is effective using small quantities of unextracted serum, allowing convenient sample collection, for example, the use of self-withdrawn blood drops by human subjects. In another aspect, the invention advantageously provides a broad-spectrum measurement of AR-based activity, representing an integrated read-out of the levels of all physiologically effective androgens in a subject or sample. The direct measurement of AR-based activity, rather than the physical measurement of each and every androgen, provides a biologically relevant measure of the physiologically effective androgen levels in a sample. For example, in animal-derived samples, the assays of the invention take into account the effects of anti-androgens and serum-binding factors.

DETAILED DESCRIPTION OF THE INVENTION

Each element of the bioassay, and various exemplary configurations thereof, will next be described in detail.

Target Hormones. "Target hormone" as used herein, refers to any natural or synthetic androgen, androgen analog or derivative, or androgen-like substance which binds a sensitive AR mutant. Exemplary target hormones include but are not limited to the natural androgens testosterone, 5-alpha-dihydrotestosterone (DHT), androstanediol, androstenedione, androstenediol, androsterone, and synthetic androgens, including fluoxymesterone, trenbolone, methyltestosterone, mestanolone, mesterolone, danazol, tibolone, tetrahydrogestrinone, oxymethalone, mibolerone, normethandrone, stanozolol, boldione, gestrinone, nandrolone, 19-norandrostenedione, as well as the metabolites of the foregoing. Target hormones include known androgens as well as unknown, uncharacterized androgens which may be detected by means of the invention, including synthetic androgen analogs and derivatives.

Generally, the invention is directed to the use of the tools and assays described herein for the detection of target hormones (e.g. androgens). It will be understood that in some alternative embodiments, the mutant AR's are also capable of binding and detecting other steroidal or non-steroidal species such as anti-androgen compounds or other naturally occurring steroids (such as progestins or estrogens).

Sensitive AR mutants. A sensitive AR mutant, as used herein, is any androgen receptor protein that is not a wild-type AR, an androgen receptor protein being defined herein as a protein that, when present in a cell, is capable of binding at least one androgen species and which is effectively translocated to the nucleus of the cell upon such binding. A sensitive AR mutant is further defined by its differential ligand binding properties, relative its corresponding wild type, the differential ligand binding properties including altered sensitivity or selectivity. Sensitive AR mutants include variants of the wild-type AR amino acid sequence of humans, mice, rats, cats, dogs, monkeys and other non-human primates, and other species. Sensitive AR mutants include AR proteins that have amino acid substitutions, deletions, additions, truncations, translocations, and other types of mutations relative to a wild-type AR sequence.

In one embodiment, the sensitive AR mutants of the invention may comprise any AR mutant that has a higher affinity for one or more target hormones than that of the wild-type AR, such that, when used in the assays of the invention, the resulting $EC_{50}$ will be lower than that obtained using like assays with a wild-type AR. In exemplary embodiments, a sensitive AR mutant is defined as one which, when used in the assays of the invention for the detection of one or more target hormones, results in an $EC_{50}$ value which is at least two-fold, three-fold, four-fold, five-fold, or more-fold lower than that obtained in like assays using the wild-type AR. The relative improvement in resulting $EC_{50}$ that defines a sensitive mutant AR may be determined with respect to a single target hormone (e.g. testosterone), or by an average sensitivity improvement with respect to a panel of selected target hormones.

The use of sensitive mutants of the invention increases the sensitivity of the prior art AR assay, allowing detection of androgens at concentrations not attainable with wild-type AR assays, and also allows for the more accurate quantification of androgens at lower concentrations than can be achieved with a wild-type AR assay.

Various AR mutants are known in the art. Exemplary sensitive AR mutants include V715M (wherein the valine at position 715 of human wild-type AR is substituted with a methionine). In the assays of the invention the V715M mutant is 7-fold more sensitive than the wild-type AR to testosterone, being equivalently more sensitive to all androgens (as described in Example 2) than the wild-type. This enables the V715M AR mutant-based assay to detect low-levels androgens even when the sample is diluted in measurement media. The V715M mutant shows some promiscuity in which the major estrogen, estradiol, is detected 127-fold better by the mutant than by the wild-type AR. However, estradiol serum levels of normal male and female humans are 3,565-fold and 9-fold, respectively, below the detection limit of the V715M assay, and substantial binding of this estrogen is not anticipated to occur or skew the measurement of androgens.

Another mutant AR known in the art is T877S (wherein the threonine at position 877 of human wild type AR is substituted with an serine). A third AR mutant known in the art is T877A (wherein the threonine at position 877 of human wild type AR is substituted with an alanine). As with V715M, these mutants show enhanced sensitivities to androgens over wild-type AR assays (with sensitivity improved 2-3-fold for all androgens in the nuclear translocation assay) with some promiscuity to non-androgenic steroids, as described in Example 2.

While the promiscuous ligand selectivity of V715M, T877S, and T877A to estradiol and progesterone are known, the inventor of the present disclosure has advantageously discovered that these mutants retain the ability to bind all androgens with much higher, relatively uniform sensitivity above that of the wild type AR, i.e. the ability to bind diverse androgens of the mutants is equivalent to that of the wild-type AR, but detection occurs at lower concentrations of ligand. Accordingly, the methods of the invention comprise the use of V715M, T877S, or T877A as sensitive AR mutants in the fusion proteins of the invention, allowing the detection and accurate quantification of low concentrations of androgens in a sample.

Advantageously, the V715M, T877S, and T877A mutants also shows increased sensitivity, but no promiscuity towards, anti-androgens currently in use (e.g. bicalutamide, enzalutimide) and under development (e.g. ARN-509). V715M, T877S, and T877A will bind to these anti-androgens but will not translocate to the nucleus, and these anti-androgens will inhibit the ability of androgens in serum to bind to and activate signal by the assay, providing a measure of physiologically effective androgen concentrations in a patient being treated with these anti-androgens. Therefore, the efficacy of such treatments in a patient can be assessed by the assay, whereas a standard testosterone assay will not detect the true physiologically effective androgen levels in a patient being treated with anti-androgens. However, there is some promiscuity of the V715M, T877S, and T877A mutant towards the anti-androgen Flutamide; it will bind these mutants and translocate to the nucleus, so the assay is not suitable in individuals being treated with this drug. However, Flutamide is no longer in widespread clinical use.

AR mutations useful for increasing sensitivity will be those that permit a uniformly enhanced binding to lowered concentrations of all androgens. Other AR mutations are known which confer survival and growth ability to prostate cancer cells in low-testosterone patients, and each such mutation may comprise a sensitive AR mutant or a promiscuous mutant, or both. A list of AR mutants is maintained as the Androgen Receptor Gene Mutations Database, as described in Gottlieb B, Beitel L K, Nadarajah A, Palioura M, Trifiro M. 2012. The Androgen Receptor Gene Mutations Database (ARDB): 2012 Update, Human Mutation 33:887-894. The ARDB may be accessed at http://androgendb.mcgill.ca. Any AR mutant associated with prostate cancer within that database may increase androgen sensitivity and mutants within or near to the AR ligand binding domain are most apt to do so. Exemplary AR mutants for use in the assays of the invention include: R630Q; K631T; S648N; E666D; Q671R; I673T; G684A; L702H; V716M; K721E; A722T; L723F; R727L; V731M; W742C; L745F; A749T; A749V; M750I; G751S; F755L; T756A; N757D; V758I; V758A; S760P; Y764C; S783N; Q799E; 1800T; R847G; V867M; E873Q; H875Y; T878A; T878S; D880G; M887I; D891N; M896V; Q903R; G910E; K911R; and Q920R.

While the exemplary sensitive AR mutants presented or referenced herein are from humans, sensitive AR mutants from other species may be utilized in the assay as well and will be deemed sensitive AR mutants to the extent they have differential specificity and selectivity for target species or have an enhanced ability to be activated by target hormones relative to their corresponding wild-type AR.

In some embodiments, a single type of sensitive AR mutant is utilized in the constructs of the invention. In an alternative embodiment, two or more types of sensitive AR mutant are utilized in a single construct or in a single assay. Multiple mutants may be expressed integrated on a single fusion protein, or may be expressed as multiple separate fusion proteins in the same cell. In one embodiment, a reporter cell expresses two or more different reporter fusion proteins, the two or more separate sensitive mutant AR reporter fusion proteins comprising distinct sensitive AR mutants. In another embodiment, distinct cell lines which express different sensitive mutant AR's are admixed when the assay is performed. Where the different species of sensitive AR mutants are used in an assay and have differing selectivity for various target hormones, the use of multiple sensitive AR mutants in a single assay expands the range of the assay.

Reporter Moiety. The invention encompasses the use of one or more suitable reporter moieties linked to the one or more sensitive AR mutants. The invention is not limited to any specific type of reporter moiety. A suitable reporter moiety is any species that is (1) capable of being translocated to the nucleus with the conjoined sensitive AR mutant; and (2) is capable of being accurately quantified in the nucleus. An exemplary reporter moiety is a fluorescent protein. Any suitable fluorescent protein may be utilized, including fluorescent proteins such as green fluorescent proteins, yellow fluorescent proteins, red fluorescent proteins, blue fluorescent proteins, etc. For example, Yellow fluorescent protein (YFP), as known in the art, may be utilized, as may improved versions of YFP such as Venus, Citrine, and YPET. Exemplary red fluorescent proteins include mCherry, mPlum, and mRaspberry. Reporter enzyme systems, utilizing a substrate which is converted to a detectable species when subject to enzyme activity, may be used as well, such as luciferase or horseradish peroxidase reporter systems. Immunolabeling systems, as known in the art, may also be used as a detection means for quantification of sensitive AR mutants localized to the nucleus.

If more than one species of sensitive AR mutant is utilized in the assay, the different species of sensitive AR mutants may be linked to a common reporter moiety, or may each be linked to a different, distinguishable reporter moiety. The use of a common reporter moiety advantageously allows for a single quantification step. The use of multiple, distinguishable reporter moieties necessitates multiple quantification steps for each, but where the differing AR mutants have differential selectivity for various species of target hormones, this enables both quantitative analysis and qualitative identification of the target hormone(s) present in the sample. Alternatively, the common reporter moiety may be used for assays in which the different types of reporter cells expressing distinct sensitive AR mutants are distinguished through the use of cell-specific markers, such as cellular 'bar-code' technologies, for example as described in Krylova et al 2013 A versatile, bar-coded nuclear marker/reporter for live cell fluorescent and multiplexed high content imaging. PLoS One. 8 (5):e63286.

Reporter Fusion Proteins. In one embodiment of the invention, the assay utilizes a reporter fusion protein comprising a sensitive AR mutant linked to a reporter moiety, referred to herein as a "reporter fusion protein." In one embodiment, the reporter fusion protein comprises a sensitive AR mutant linked to a fluorescent protein. The linkage may be of any nature, including reporter moieties linked to the C-terminus or N-terminus of the AR mutant. Spacers may optionally be utilized to separate the two elements of the construct, for example spacers of 5-15 amino acids, for example, a spacer comprising the sequence KDPPVAT (SEQ ID: 1) or SGLRSRAT (SEQ ID: 2). Fusion proteins comprising a sensitive AR mutant and two or more reporter moieties may also be used, for example, comprising a sensitive AR mutant flanked by two reporters. In such embodiments, the two or more reporters may comprise the same reporter moiety, in order to boost signal. In other embodiments, two or more distinct reporter moieties (e.g. different types of fluorescent proteins) are linked to the sensitive AR mutant.

Exemplary reporter fusion proteins of the invention comprise sensitive AR mutants which are fused to two yellow fluorescent proteins (YFP), one YFP linked to the amino terminus and one YFP linked to the carboxyl terminus of the sensitive AR mutant protein. For example, YFP-V715M-YFP is a fusion protein comprising the mutant AR V715M flanked between two YFP's, the amino acid sequence of which is denoted by SEQ ID: 3. Another fusion protein of the invention is YFP-T877S-YFP, which is a fusion protein comprising the sensitive mutant AR T877S flanked between two YFP's, the amino acid sequence of which is denoted by SEQ ID: 4. A third fusion protein of the invention is YFP-T877A-YFP, which is a fusion protein comprising the sensitive AR mutant T877A flanked between two YFP's, the amino acid sequence of which is denoted by SEQ ID: 5.

Reporter Polynucleotide Constructs. The invention comprises not only the reporter fusion proteins described herein, but further includes any polynucleotide constructs coding therefor (referred to herein as "reporter polynucleotide constructs"). Such nucleotide sequences may comprise cloning vectors, expression vectors, plasmids, expression cassettes, or transformed cells. Exemplary nucleotide sequences of the invention include SEQ ID: 6 which codes for the fusion protein YFP-V715M-YFP; SEQ ID: 7, which codes for the fusion protein YFP-T877S-YFP; and SEQ ID: 8, which codes for the fusion protein YFP-T877A-YFP.

Reporter Cells. A polynucleotide construct encoding a reporter fusion protein of the invention is expressed in a cell, the transduced cell being referred to herein as a "reporter cell". The reporter polynucleotide constructs may be introduced into the target cell by any means known in the art. Exemplary methods for introducing reporter polynucleotide constructs to target cells include viral transfection (e.g. using Adeno or Adeno-associated virus); chemical transformation methods (e.g. DEAE-dextran, polyethyleneimine, dendrimer, polybrene, calcium phosphate, lipofectin, DOTAP, lipofectamine, or CTAB/DOPE, DOTMA); or physical methods (e.g. injection, biolistic bombardment, or laser assisted transduction, micro-needle, Gene Gun, etc.), as known in the art. The fusion proteins may be expressed under the control of any promoter, including constitutive promoters, such as that from the human cytomegalovirus. Other exemplary constitutive promoters include the EF1a, SV40, PGK1 or Ubc promoters, as known in the art. Polynucleotide sequences coding for such promoters may be included in polynucleotide reporter constructs of the invention.

In one embodiment, the polynucleotide reporter constructs of the invention are stably integrated in the reporter cell. The use of stably integrated reporter polynucleotide constructs advantageously allows for consistent expression of reporter fusion proteins among clonal batches of reporter cells. Alternatively, the reporter fusion proteins of the invention may be transiently expressed in a reporter cell, utilizing methods of transient gene expression known in the art. In another alternative embodiment, the fusion proteins of the invention are applied to the reporter cells exogenously, for example utilizing exogenous protein delivery methods known in the art, such as biodegradable nanoparticle encapsulation delivery vehicles or agents such as the BIO-PORTER™ Protein Delivery Reagent (Amsbio Inc.).

The reporter cell may be of any type capable of properly expressing the reporter fusion proteins of the invention, translocating them to the nucleus upon binding of a target hormone, and allowing accurate quantification of the reporter moiety. The reporter cell may be any cell, including cells within transformed organisms or cells in culture. Human or human-derived reporter cells may be utilized, as well as reporter cells from other eukaryotic species, including mammalian cell lines. Exemplary human-derived cell lines include HeLa cells, PC3 prostate cancer cells, NCI60 cells, DU145 cells, U87 cells, LNCaP-C4-2 cells, HEK293T, and MCF-7 cells and other human-derived cell lines known in the art. Exemplary non-human reporter cells include yeast, murine, rat, lupine, canine, and primate cells.

Nuclear Labeling Construct. Some aspects of the invention encompass a nuclear labeling construct. The nuclear labeling construct may be utilized generally in nuclear translocation assays, including the sensitive mutant AR assays of the invention. Numerous nuclear translocation assays are known in the art, wherein a biological species (e.g. a receptor, a growth factor, etc.) conjugated to a reporter moiety (or conjugated to reporter gene activating elements), upon some biological event such as ligand binding or phosphorylation, is translocated to the nucleus and the resulting reporter moiety signal in the nucleus is quantified to determine the amount of translocated biological species. For example, nuclear translocation assays known in the art include the NF-κB translocation assay, the glucocorticoid receptor translocation assay, the ERK-MAPK translocation assay, and others. These assays typically rely on nuclear staining dyes such as Hoechst 33342 or DAPI to delineate the nucleus for accurate quantification of the translocated reporter moiety. However, as disclosed herein, the use of a nuclear labeling construct which is expressed in the cells of the assay provides a facile method of delineating the nucleus without the additional, error prone staining step. Accordingly, the invention comprises cells capable of performing a nuclear localization assay, wherein a nuclear labeling construct is expressed. The invention further includes methods of performing any nuclear translocation assays with such cells.

The nuclear labeling construct may comprise a nuclear labeling fusion protein that labels the nucleus of the cell in which it is expressed, which aids in the imaging and delineation of the nucleus. When used in conjunction with a nuclear translocation assay, the nuclear labeling fusion protein advantageously allows for the facile quantification of nuclear-translocated reporter moieties. The nuclear labeling constructs of the invention further include polynucleotides which code for such fusion proteins.

The nuclear labeling fusion protein comprises a nuclear localization element linked to one or more reporter moieties. Any number of nuclear localization elements known in the art may be utilized, for example the SV40 large T antigen nuclear localization signal. Other nuclear localization signals include the SV40 medium T-antigen, the influenza virus nuclear localization signal, and viral Tat proteins such as HIV Tat. Additional nuclear localization signals include those described in Lange et al., Classical Nuclear Localization Signals: Definition, Function, and Interaction with Importin α, 2007 The Journal of Biological Chemistry, 282, 5101-5105 or in Nair et al., NLSdb: database of nuclear localization signals, Nucl. Acids Res. (2003) 31 (1): 397-399.

The nuclear localization signals are linked to one or more reporter moiety. Any reporter moiety may be used, such as green fluorescent proteins, yellow fluorescent proteins, red fluorescent proteins, and blue fluorescent proteins. Exemplary nuclear markers include mCherry, mPlum, mRaspberry, Venus, Citrine, and YPET. Combinations of fluorescent proteins may be used, creating unique spectral signatures. This is especially useful when multiple admixed distinct cell lines are used in the assay. For example, different pairings of mCherry, mPlum, mRaspberry, or all three in combination may be used as the one or more reporter moiety.

When used in combination with a nuclear translocation assay, generally, it will be advantageous for the reporter moiety of the nuclear localization signal construct to be one that that can be effectively distinguished from the reporter moiety utilized on the translocated species to be measured, in order to avoid signal noise or overlap.

In one embodiment, a nuclear translocation assay is carried out using two or more distinct cell lines, each such cell line expressing a different receptor or other translocated species, wherein each distinct cell line expresses a distinct nuclear localization construct reporter moiety. Using spectrally distinct nuclear labeling moieties (for example, mPlum, mRaspberry and mCherry, or combinations thereof) in different cell lines permits each cell line to be measured distinctly when such different reporter cell lines are mixed and exposed to the same sample.

In one embodiment, the nuclear localization construct is utilized in performing any nuclear localization assay. In one embodiment, the nuclear localization construct is utilized in reporter cells of the sensitive AR mutant assays described herein. In one embodiment, the invention comprises a reporter cell expressing a sensitive AR mutant linked to yellow fluorescent protein and also expressing a nuclear localization construct comprising an SV40 large T antigen nuclear localization sequence linked to two mPlum fluorescent proteins, the YFP and mPlum signals being easily distinguished.

Alternative Configuration. In an alternative configuration, the reporter moiety and the sensitive AR mutant are not linked. Instead, a gene sequence coding for the sensitive AR mutant is expressed in the reporter cell. Additionally, a gene sequence coding for the reporter moiety is present in the reporter cell, under the control of a promoter comprising one or more AR response element, optionally in conjunction with a minimal promoter. When the sensitive AR mutant binds a target hormone and translocates to the nucleus, it will bind the hormone response element linked to the reporter gene and promote the expression of the reporter moiety. In some implementations, the DNA binding domain of the sensitive AR mutant may be replaced by a different DNA binding domain with a unique response element, which such response element can be used to induce reporter gene expression in the presence of target-hormone bound mutant AR. In one embodiment, the reporter may be expressed under the control of promoter fragment from androgen-regulated genes, such as the genes for prostate-specific antigen. In another embodiment, one or more AR response elements, comprising or similar to the consensus AR-binding DNA sequence of SEQ ID: 9, are appended to a reporter gene promoter to allow the translocated sensitive mutant AR to bind and impart androgen-regulation of the gene.

Derivatives and Functional Equivalents. It will be understood by one of skill in the art that the scope of the invention is not limited to the exemplary protein and polynucleotide sequences disclosed or referenced herein and that the invention further encompasses the use of functional equivalents of referenced or disclosed sequences. For example the invention includes protein sequences comprising truncations, deletions, amino acid substitutions, and other variants of the protein sequences disclosed herein where the variant fusion protein has substantially similar functional properties to those of the fusion protein from which the variant protein is derived. Likewise, the invention includes polynucleotide sequences comprising truncations, deletions, nucleotide substitutions, and other variants of the polynucleotide sequences disclosed herein where the variant sequence codes for a fusion protein having substantially similar functional properties to those of the fusion protein coded by the polynucleotide sequence from which the variant polynucleotide sequence is derived. For example, it will be understood that the redundancy of the genetic code allows for multiple polynucleotide sequences to code for identical or substantially identical reporter fusion proteins. Furthermore, it will be understood that there are differential codon preferences, post-transcriptional modifications, and post-translational modifications among different species, and that the invention encompasses substitution and modifications to the mutant AR nucleotide sequences from one species in order to optimize their expression in heterologous hosts.

Assay Performance. When utilizing broad-spectrum and sensitive AR mutants, for example V715M, T877A, or T877S mutants, the assays of the invention retain specificity for androgens that parallels that of the wild-type AR, but can detect them at lower concentration. Because the assays of the invention integrate the effects of all androgens, as well as the effects of serum binding factors on androgen availability, they provide an improvement over measurement of the concentration of a single androgen (e.g. testosterone) extracted from the serum.

In general, the fusion proteins and assay systems of the invention are utilized to identify the presence of target hormones (qualitative assay) and/or to quantify the amount of target hormones in a sample (quantitative assay). Samples may comprise environmental samples or may comprise samples derived from an animal, including a research animal, a veterinary patient, or a human subject. An exemplary sample is a bodily fluid, including blood, serum, urine, saliva, or sweat. Samples may be concentrated or diluted, as known in the art, as necessary to reach a minimum concentration of target hormone in the sample that is within the effective concentration range of the assay, for example, in the range of 1-1,000 ng/dL. The use of the higher sensitivity mutants circumvents the need to concentrate the sample and thereby enables measurement to be conducted directly on the sample without prior processing steps.

A preferred bodily fluid for assaying target hormones is serum. Serum measurements of target hormone concentration are generally more reproducible than measurements from urine. However, currently-used wild-type AR-based assays are not sensitive enough to accurately measure low levels of target hormones in serum, for example, testosterone as found in the serum of females or in the serum of androgen-suppressed males with prostate cancer. Advantageously, the ultrasensitive assays of the invention can accurately measure such low concentrations, for example in the range of 1-20 ng/dL, and may do so with small samples without a need for concentration of the sample. For example, a fraction of a drop of serum (5 μl) is sufficient to measure target hormones in the assays of the invention. This advantageously allows for self-collection (for example, at home) of samples by human subjects, for example collection of a blood drop with a finger prick, rather than an expensive and inconvenient clinical blood draw.

In another implementation, the methods of the invention may be applied to urine. For urine measurements, two factors must be taken into account. The first is that urine itself may affect the strength of the measured signal of the reporter moiety. Where urine affects the signal strength of the reporter moiety, this effect must be quantified and applied as a correction factor.

For example, YFP fluorescence measured in the cell nuclei of urine-treated reporter cells represents both the effects of target hormone-bound nuclear-translocated mutant AR-YFP, and also the independent effects of urine on the fluorescence properties of YFP. YFP fluorescence in reporter cell nuclei reaches a maximum when exposed to saturating levels of target hormone, for example, testosterone at about $10^{-7}$M, in the absence of urine. If urine is added to the reporter cells in addition to the saturating levels of target hormone, the level of background-subtracted YFP fluorescence is increased yet further, by 0 to 24% depending on the urine sample, demonstrating a sample-specific direct amplification effect of urine on YFP fluorescence. Because the effect varies among samples, two aliquots of each sample are required. A first aliquot is used to determine the sample-specific urine-induced percentage increase in the physical fluorescence properties of YFP in the presence of saturating testosterone ("correction factor"). A second sample aliquot is assayed using the methods of the invention. The correction factor is used to subtract the percentage increase from the YFP fluorescence signal measurement of the second aliquot. The corrected YFP fluorescence of the sample then is used to extrapolate the target hormone levels from a standard curve.

When utilizing urine as the sample bodily fluid, another factor to take into account is that testosterone and other androgens, when metabolized in the body, may be modified by glucuronidation or sulfonation and then excreted into the urine. For example, testosterone is predominantly found in urine as a conjugate with glucuronic acid in the form of testosterone-β-D-glucuronide. Androgens so modified by metabolic processes are generally not detectable by AR-based assays. Therefore urine samples should be pre-treated by incubation with glucuronidase and arylsulfatase to release target hormones from metabolic conjugates, utilizing methodologies as known in the art.

Target hormone levels are assessed by first exposing a group of reporter cells to a sample putatively containing a target hormone. Any number of cells may be utilized in the assay, for example 100 to 1,000,000 cells may be exposed to the sample. In one implementation, 500 to 5,000 cells are utilized. For example, using a standard 384-well dish, about 2500 reporter cells may be plated per well in about 30 µl of cell culture media, and a sample, for example, in the range of 1-5 µl in volume may be introduced.

Next, the cells and the sample are allowed to incubate, during which time target hormones present in the sample will diffuse into the reporter cells. Upon binding the sensitive mutant AR fusion proteins present in the cytoplasm, the sensitive mutant AR fusion protein and bound target hormones will translocate to the nucleus, and reporter moiety will accumulate there at a magnitude proportional to the amount of target hormone in the sample. The incubation period may be any period sufficient for measurable translocation of the fusion protein, for example from one to thirty hours, for example, from 18 to 24 hours. The mutant AR fusion protein translocation typically reaches steady state within five hours of sample addition.

After the incubation period, the amount of nuclear mutant-AR linked reporter moiety in the nuclei of the reporter cells is quantified. Any number of nuclei may be assessed, such that an accurate, representative sampling of the exposed cells is performed. For example, 10 to 500 nuclei may be imaged and reporter moiety quantified therein. In one embodiment, at least 40 nuclei are assessed. The quantification of reporter moiety in the nucleus may be performed using methodologies and instrumentation as appropriate for the type of reporter moiety used, as known in the art. For example, if the reporter moiety is a fluorescent protein, quantification may be effected by standard fluorescent microscopy techniques. For example, images using spectral modalities that capture signal from the sensitive mutant AR-bound reporter moiety are captured. If a nuclear marker or nuclear dye are used, images capturing such are obtained utilizing the appropriate spectral modality. Image analysis software such as MetaXpress™ available with the IXMicro high throughput microscopy platform (Molecular Devices), or similar systems known in the art, may be used.

Quality control measurements establish the reliability of the quantification of the average levels of sensitive mutant AR-linked reporter in the cell nucleus. For example, fields that have less than 40 cells may be considered unreliable. In another quality control assessment, the signal (e.g. fluorescence) of the nuclear marker, which does not change intensity upon androgen addition, is used to define erroneous fields in which the average nuclear marker signal (e.g. fluorescence) deviates more than three standard deviations from the mean measured in all fields. In another quality control embodiment, the amount of sensitive mutant AR-linked reporter signal in the nuclei of cells is measured within two different fields within each well. Wells in which the mutant AR-linked reporter measurements deviate from each other by more than a defined level (for example, 20%) are considered to be suspect. Replica measurements on each sample are usually conducted in multiple wells (for example, four wells), with the quantity of nuclear, mutant AR-linked reporter moiety signal averaged from all wells that pass the quality control criteria.

Finally, the measured quantity of nuclear, mutant AR-linked reporter moiety signal observed in the assayed cells may be compared to a standard curve generated using like cells, like cell quantities, and like measurement operations as used in the assayed cells. The curve allows the extrapolation of the amount of target hormone in the sample. The standard curve is generated as known in the art, by measuring nuclear sensitive mutant AR-linked reporter moiety signal in groups (e.g. wells) of reporter cells that have been exposed to known concentrations of target hormone. In one embodiment of the assay, the androgen used for the standard curve is testosterone. The sum total of all activities influencing sensitive mutant AR activity then are reported as 'testosterone-equivalents' of androgen activity. Those concentrations of androgens are then multiplied by the assay dilution factor (for example, 5 µl of serum added to 30 µl of media within each well represents a seven-fold dilution). Finally, using these measurements, the concentration of target hormones in the sample is calculated.

The assays of the invention may be utilized in any number of analytical, research, or medical applications. For example, the assays of the invention may be utilized in: assessing testosterone levels in male patients being diagnosed or treated for testosterone deficiency; in male patients being treated for prostate cancer; in male patients undergoing androgen suppression treatment, for example to assess the efficacy or treatment or to adjust dosages; in screening assays for identifying putative androgen suppression molecules; for quantifying the efficacy of androgen suppression molecules; in female patients being diagnosed or treated for polycystic ovary disease; in monitoring androgen levels in patients receiving hormonal therapies as part of gender reassignment procedures; and in other procedures.

Advantageously, when using broad-spectrum sensitive AR mutants (e.g. V715M, T877S, and T877A) the assay serves as a functional assay to identify the presence of any number of substances or factors that may influence androgenic activity. For example, the level of anti-androgen therapeutics provided to a patient to effectively limit the effectiveness of the subject's androgens will impact the bioassay measurement and provide details about the effectiveness of anti-androgens at the dose provided. For example, serum sex hormone binding globulins will alter the availability of androgens in serum samples. The bioassay of the invention will measure the cumulative androgen activity level affected by all factors present in the subject's serum. Accordingly, the assays of the invention may be applied in broadly monitoring for both known and unknown androgens and non-androgenic influences on androgenic activity.

For example, the presence of known and unknown anabolic androgenic steroids in athletes may be monitored. Current methods for detecting the presence of natural or synthetic androgens in serum and urine are based upon immunoassays or mass spectrometry. Both measurements rely on prior knowledge of the androgens so that they may be specifically detected. Athletes with a strong interest in circumventing the monitoring methods can escape detection by using compounds currently not detected or by doping with testosterone. The broad-spectrum assays of the invention will allow detection of such banned practices by measuring total androgenic activity of factors present in the subject's serum or other bodily fluid.

Further, the ability to broadly test for androgenic substances is advantageous in environmental monitoring. The assays of the invention allow detection in the environment of low levels of naturally-occurring, excreted, or industrial androgenic or anti-androgenic substances of known and unknown chemical structure. The current assay provides such an increase in throughput and such a dramatic reduction in cost, and through the use of finger-prick blood samples or urine samples the convenience of self-collection, that the large-scale sampling required for environmental monitoring becomes feasible. For example the androgenic status of the general population may be inexpensively assessed to determine exposure to environmental androgens. Environmental samples may be abiotic, such as soil-derived samples, or water samples such as groundwater or water from rivers, lakes, or streams. The environmental samples may comprise biotic samples from organisms, such as animals. The androgenic status of wild animals to monitor the presence or action of environmental androgens, or the action of anti-androgenic factors, is also enabled by the use of the invention, as the novel assays require very small bodily fluid samples. In contrast, the currently-used detection methods require large volumes of bodily fluids, the collection of which is problematic in small animals.

EXAMPLES

Example 1

AR assay utilizing the V715M sensitive AR mutant linked to YFP. Reporter cells were generated by stably integrating a CFP-V715M AR-YFP polynucleotide construct in HeLa cells. As a control, a reporter cell comprising a wild-type human CFP-AR-YFP construct was also generated. In both reporter cell types, the CFP-AR-YFP construct was expressed under the control of a CMV constitutive promoter. Only YFP fluorescence is measured for AR quantification since the amount of CFP fluorescence lost to energy transfer changes with androgens in these reporters (Schaufele et al, 2005 The structural basis of androgen receptor activation: intramolecular and intermolecular amino-carboxy interactions Proc Natl Acad Sci USA 102 (28):9802-7). Both reporter cell types also expressed mCherry or mPlum red fluorescent protein linked to an SV40 large T antigen nuclear localization signal and nuclei in both reporter cells were clearly visible by imaging that fluorescence. For each reporter cell, a standard curve was generated by applying testosterone in varying concentrations to batches of each cell (e.g. about 2,500 cells per batch, each in a well of a 348 well plate) and measuring YFP fluorescence in the nuclei. The half-maximal effective concentration ($EC_{50}$) demonstrated the V715M AR-YFP reporter cells to be about seven fold more sensitive than the wild-type AR-YFP reporter cells, demonstrating a substantial increase in the sensitivity of the V715M AR-YFP reporter cells for testosterone, as well as for other androgens (as described in Example 2). The increase in sensitivity was sufficient to substantially extend the range of measurement accuracy to within the normal range of testosterone concentrations in women. Further, the sensitivity of the V715M AR-based assay is sufficient to allow detection of testosterone at levels normally observed in androgen-suppressed prostate cancer patients, whereas the wild-type AR-YFP is not sufficiently sensitive to detect testosterone at these low concentrations.

Example 2

Specificity of mutant AR bioassays. A wild-type YFP-AR-YFP reporter cell and reporter cells expressing CFP-V715M-YFP, CFP-T877S-YFP, and CFP-T877A-YFP constructs were generated, as in Example 1. Each cell type was exposed to a suite of androgens and other steroid hormones at varying concentrations, and resulting YFP signal localized to the nucleus was measured. An $EC_{50}$ for each androgen was calculated for each reporter cell type. The log EC50 values demonstrated that all three sensitive mutant AR assays were consistently effective in detecting the same androgens detected by the wild type receptor, with 3 to 7 fold or more greater sensitivity. Most non-androgen steroids were not detected or were poorly detected by the wild-type AR. All non-androgen hormones were detected by the wild-type and mutant androgen receptors only at concentrations that exceed the range of concentrations normally found in human serum.

Example 3

Measurement of Serum Androgen Levels in Females. Reporter cells expressing CFP-T877S-YFP and an mPlum-nuclear localization signal construct were generated as described in Example 1. Forty serum samples that contain androgen levels spanning the 'normal' concentrations in females and males were obtained from the United States Centers for Disease Control (CDC) Hormone Standardization (HoSt) Program. These samples represent the standards against which clinical diagnostic laboratories assess their measurement of testosterone extracted from serum against the rigorously determined measurements on the same samples conducted by the CDC HoSt laboratory. The T877S AR-YFP reporter cells were used to measure total serum androgens (6-7 independent measurements for each sample), and the results showed excellent day-to-day reproducibility. The serum androgen levels measured are typically less than that of the well-calibrated concentrations of testosterone extracted from serum, particularly in male samples where androgens are present at concentrations that will be bound by sex hormone binding globulins. In two of twenty female samples, available androgens measured by the assay of the invention exceeded that of the testosterone measurement suggesting that testosterone-only values may not be capturing the entire androgen burden in some individuals. Studies of female patients (See Example 5) suggest that the accurate measurement of all serum androgens permitted by the ultrasensitive assay correlates better with clinical presentation that does measurement of just testosterone extracted from serum.

Example 4

Detection of serum androgens in androgen-suppressed prostate cancer patients. Males undergoing androgen-suppression therapy as a part of prostate cancer treatment have extremely low levels of androgens. Testosterone is not typically measured in such patients. Utilizing the CFP-T877S-YFP reporter cells and serum measurement methods described herein, androgens in the serum of 5 male patients undergoing androgen suppression therapy was detected and quantified against a testosterone standard curve. The observed androgen concentrations in the five patients ranged from about 3-18 ng of testosterone equivalent activity/dl. Serum samples were obtained from the same five patients after they were further treated with an additional androgen suppression treatment (a Cyp17 inhibitor). The T877S AR-YFP reporter cells detected a drop in serum testosterone to a range of 0.5-9 ng/dl in response to Cyp17 inhibitor treatment.

Example 5

The ultrasensitive assay of the invention provides an improved assessment of polycystic ovary syndrome (PCOS). Excess androgens represent one of the diagnostic criteria of PCOS. CFP-T877S-YFP reporter cells, as described above, were utilized to measure androgens in PCOS patients. Testosterone measurements on the same samples were conducted by the PCOS clinic using standard methods (mass spectrometry or immunoassay) ordered by the attending physician as clinically necessary for the evaluation of the patient. The measurement of testosterone extracted from serum using the standard assays did not correlate cleanly with PCOS symptoms. By contrast, the measurement of all serum androgens by the T877S AR-YFP reporter cells provided an improved assessment of PCOS: using the assay of the invention, mean androgen concentration in PCOS patients was elevated relative to control subject, whereas testosterone levels measured using the standard assay were not as able to effectively discriminate between PCOS patients and control subjects. With the poor assessment of PCOS by the standard testosterone assay, clinical evaluation of PCOS also relies on other dermatologic evidence of androgen excess, including elevated body hair density (hirsutism), reduced scalp hair density and severity of acne. Androgen measurement by the T877S AR-YFP reporter cells provided a statistically improved association with the dermatologic assessment of the extent of hirsutism than does the standard testosterone measurement, which did not correlate at all with hirsutism.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of assessing the concentration of physiologically effective androgens in a sample derived from an animal, comprising the steps of:
    exposing a plurality of reporter cells to a sample derived from an animal having unknown levels of physiologically effective androgens, wherein each reporter cell expresses one or more ultrasensitive mutant AR's and one or more reporter moieties, and wherein the magnitude of reporter moiety signal in the nucleus is proportional to the concentration of androgen-bound ultrasensitive mutant AR's translocated to the nucleus;
    incubating the reporter cells and the sample for a period of time sufficient for androgenic substances in the sample to diffuse into the reporter cells and bind to the ultrasensitive mutant AR's, and for the androgen-bound ultrasensitive mutant AR's to translocate to the reporter cell nuclei;
    measuring the magnitude of the reporter moiety signal in a representative sample of reporter cell nuclei;
    comparing the measured reporter moiety signal to that observed in like cells exposed to a range of known concentrations of a standard androgen, in order to estimate the concentration of physiologically effective androgens in the sample, wherein the physiologically effective androgen measurement accounts for the effects of androgen binding factors.

2. The method of claim 1, wherein
each of the one or more ultrasensitive AR mutants is sufficiently sensitive that its use in an AR nuclear translocation assay or AR-regulated promoter assay for testosterone results in at least a 2-fold lower $EC_{50}$ value than that obtained for a like nuclear translocation assay for testosterone that utilizes the wild-type AR.

3. A method of assessing the concentration of physiologically effective androgens in a sample, comprising the steps of:
    exposing a plurality of reporter cells to a sample having unknown levels of physiologically effective androgens, wherein each reporter cell expresses one or more ultrasensitive mutant AR's and one or more reporter moieties, and wherein the magnitude of reporter moiety signal in the nucleus is proportional to the concentration of androgen-bound ultrasensitive mutant AR's translocated to the nucleus;
    incubating the reporter cells and the sample for a period of time sufficient for androgenic substances in the sample to diffuse into the reporter cells and bind to the ultrasensitive mutant AR's, and for the androgen-bound ultrasensitive mutant AR's to translocate to the reporter cell nuclei;
    measuring the magnitude of the reporter moiety signal in a representative sample of reporter cell nuclei; and
    comparing the measured reporter moiety signal to that observed in like cells exposed to a range of known concentrations of a standard androgen, in order to estimate the concentration of physiologically effective androgens in the sample, wherein the concentration of physiologically effective androgens in the sample is in the range of 1-20 ng/dl.

4. The method of claim 1, wherein
the ultrasensitive AR mutant comprises V715M, T877S, or T877A.

5. The method of claim 1, wherein
the one or more reporter moieties is expressed in a fusion protein wherein it is linked to the ultrasensitive mutant AR.

6. The method of claim 1, wherein
the one or more reporter moieties is expressed under the control of a promoter that is activated by androgen-bound ultrasensitive AR mutant.

7. The method of claim 1, wherein
the one or more reporter moieties comprises a fluorescent protein.

8. The method of claim 7, wherein
the fluorescent protein is yellow fluorescent protein.

9. The method of claim 1, wherein
the volume of the sample comprises between 1 and 10 µl.

10. The method of claim 1, wherein
the sample is derived from a human subject.

11. The method of claim 10, wherein
the sample comprises blood, serum, sweat, or urine.

12. The method of claim 1, wherein
the sample is not concentrated.

13. The method of claim 1, wherein
the reporter cell further expresses a nuclear marker linked to a nuclear localization signal, wherein the nuclear marker signal is distinguishable from that of the one or more reporter moieties.

14. The method of claim 13 wherein
the nuclear marker comprises one or more fluorescent proteins, the one or more fluorescent proteins generating signal that is spectrally distinct from the signal generated by the reporter moiety.

15. The method of claim 3, wherein
the ultrasensitive AR mutant comprises V715M, T877S, or T877A.

* * * * *